US009486435B2

(12) United States Patent
Hinman et al.

(10) Patent No.: US 9,486,435 B2
(45) Date of Patent: Nov. 8, 2016

(54) (HET)ARYL-P-QUINONE DERIVATIVES FOR TREATMENT OF MITOCHONDRIAL DISEASES

(71) Applicant: Edison Pharmaceuticals, Inc., Mountain View, CA (US)

(72) Inventors: Andrew W. Hinman, San Francisco, CA (US); Kieron E. Wesson, Burlingame, CA (US)

(73) Assignee: Edison Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 14/586,516

(22) Filed: Dec. 30, 2014

(65) Prior Publication Data

US 2015/0297551 A1 Oct. 22, 2015

Related U.S. Application Data

(62) Division of application No. 12/811,694, filed as application No. PCT/US2009/030229 on Jan. 6, 2009, now Pat. No. 8,952,071.

(60) Provisional application No. 61/010,387, filed on Jan. 8, 2008, provisional application No. 61/010,409, filed on Jan. 8, 2008.

(51) Int. Cl.
*A61K 31/122* (2006.01)
*A61K 31/277* (2006.01)
*C07C 50/28* (2006.01)
*C07C 255/56* (2006.01)
*C07D 307/80* (2006.01)

(52) U.S. Cl.
CPC ........... *A61K 31/277* (2013.01); *A61K 31/122* (2013.01); *C07C 50/28* (2013.01); *C07C 255/56* (2013.01); *C07D 307/80* (2013.01); *C07C 2101/16* (2013.01)

(58) Field of Classification Search
CPC ................... A61K 31/277; A61K 31/122
USPC ........................................... 514/688
See application file for complete search history.

(56) References Cited

U.S. PATENT DOCUMENTS

| 5,801,159 | A | 9/1998 | Miller et al. |
|---|---|---|---|
| 6,232,060 | B1 | 5/2001 | Miller et al. |
| 6,426,362 | B1 | 7/2002 | Miller et al. |
| 6,528,042 | B1 | 3/2003 | Brown et al. |
| 6,608,196 | B2 | 8/2003 | Wang et al. |
| 6,653,346 | B1 | 11/2003 | Wang et al. |
| 7,034,054 | B2 | 4/2006 | Miller et al. |
| 7,078,541 | B2 | 7/2006 | Boddupalli et al. |
| 7,119,117 | B2 | 10/2006 | Beinlich et al. |
| 7,179,928 | B2 | 2/2007 | Smith et al. |
| 7,393,662 | B2 | 7/2008 | Heavner et al. |
| 7,432,305 | B2 | 10/2008 | Miller et al. |
| 7,470,798 | B2 | 12/2008 | Wang et al. |
| 7,491,312 | B2 | 2/2009 | Gilat et al. |
| 7,514,461 | B2 | 4/2009 | Wang et al. |
| 7,718,176 | B2 | 5/2010 | Heavner et al. |
| 7,875,607 | B2 | 1/2011 | Wang et al. |
| 7,968,746 | B2 | 6/2011 | Jankowski et al. |
| 8,044,097 | B2 | 10/2011 | Wang et al. |
| 8,106,223 | B2 | 1/2012 | Wesson et al. |
| 8,314,153 | B2 | 11/2012 | Miller et al. |
| 8,952,071 | B2 * | 2/2015 | Hinman ................. C07C 50/28 514/688 |
| 2002/0132845 | A1 | 9/2002 | Miller et al. |
| 2003/0022818 | A1 | 1/2003 | Miller et al. |
| 2003/0144219 | A1 | 7/2003 | Phinney et al. |
| 2005/0065099 | A1 | 3/2005 | Walkinshaw et al. |
| 2005/0067303 | A1 | 3/2005 | Wong et al. |
| 2006/0281809 | A1 | 12/2006 | Miller et al. |
| 2007/0225261 | A1 | 9/2007 | Miller et al. |
| 2009/0162890 | A1 | 6/2009 | Gilat et al. |
| 2009/0163529 | A1 | 6/2009 | Gilat et al. |
| 2009/0291092 | A1 | 11/2009 | Miller et al. |
| 2010/0010100 | A1 | 1/2010 | Hinman et al. |

(Continued)

FOREIGN PATENT DOCUMENTS

EP 0 065 368 A1 11/1982
JP 2008-542389 A 11/2008

(Continued)

OTHER PUBLICATIONS

Pfeffer G, Majamaa K, Turnbull DM, Thorburn D, Chinnery PF. Treatment for mitochondrial disorders. Cochrane Database Syst Rev. 2012, Issue 4. Art. No. CD004426.DOI:10.1002/1451858. CD004426.pub.3.*
NINDS Friedreich's Ataxia Information Page. http://www.ninds.nih.gov/disorders/friedreichs_ataxia/friedreichs_ataxia.htm. 2014.*
NINDS Alzheimer's Disease Information Page. http://www.ninds.nih.gov/disorders/alzheimersdisease/alzheimersdisease.htm. 2015.*
NINDS Parkinson's Disease Information Page. http://www.ninds.nih.gov/disorders/parkinsons_disease/parkinsons_disease.htm. 2015.*

(Continued)

*Primary Examiner* — Jennifer M Kim
(74) *Attorney, Agent, or Firm* — Squire Patton Boggs (US) LLP

(57) ABSTRACT

Methods of treating or suppressing mitochondrial diseases, such as Friedreich's ataxia (FRDA), Leber's Hereditary Optic Neuropathy (LHON), mitochondrial myopathy, encephalopathy, lactacidosis, stroke (MELAS), Kearns-Sayre Syndrome (KSS), are disclosed, as well as compounds useful in the methods of the invention, such as 2-(3-hydroxy-3-methyl-butyl)-6-(het)aryl-p-quinone or as 2-(3-hydroxy-3-methylbutyl)-3-(het)aryl-p-quinone derivatives. Energy biomarkers useful in assessing the metabolic state of a subject and the efficacy of treatment are also disclosed. Methods of modulating, normalizing, or enhancing energy biomarkers, as well as compounds useful for such methods, are also disclosed.

17 Claims, No Drawings

(56) References Cited

U.S. PATENT DOCUMENTS

| | | |
|---|---|---|
| 2010/0029784 A1 | 2/2010 | Hinman et al. |
| 2010/0056429 A1 | 3/2010 | Miller et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0142834 A1 | 6/2011 | Miller |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2011/0269776 A1 | 11/2011 | Miller |
| 2012/0088783 A1 | 4/2012 | Wang et al. |
| 2012/0101169 A1 | 4/2012 | Hawi |
| 2012/0122934 A1 | 5/2012 | Jankowski et al. |
| 2012/0122969 A1 | 5/2012 | Miller |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0345312 A1 | 12/2013 | Jankowski et al. |
| 2014/0275045 A1 | 9/2014 | Hinman et al. |
| 2014/0275054 A1 | 9/2014 | Hinman et al. |
| 2015/0216820 A1 | 8/2015 | Miller et al. |
| 2015/0218079 A1 | 8/2015 | Shrader et al. |

FOREIGN PATENT DOCUMENTS

| | | |
|---|---|---|
| JP | 2009-527567 A | 7/2009 |
| WO | WO-03/064403 A1 | 8/2003 |
| WO | WO-2004/003565 A2 | 1/2004 |
| WO | WO-2004/003565 A3 | 1/2004 |
| WO | WO-2006/130775 A2 | 12/2006 |
| WO | WO-2006/130775 A3 | 12/2006 |
| WO | WO-2007/100652 A2 | 9/2007 |
| WO | WO-2007/100652 A3 | 9/2007 |
| WO | WO-2008/002641 A2 | 1/2008 |
| WO | WO-2008/002641 A3 | 1/2008 |
| WO | WO-2011/041452 A2 | 4/2011 |
| WO | WO-2011/113018 A1 | 9/2011 |
| WO | WO-2012/019029 A2 | 2/2012 |
| WO | WO-2012/019032 | 2/2012 |
| WO | WO-2012/154613 | 11/2012 |
| WO | WO-2012/170773 | 12/2012 |
| WO | WO-2012/174286 | 12/2012 |
| WO | WO-2013/006736 | 1/2013 |
| WO | WO-2013/006737 | 1/2013 |
| WO | WO-2013/013078 | 1/2013 |
| WO | WO 2014145116 | 9/2014 |
| WO | WO 2014145118 | 9/2014 |
| WO | WO 2014194292 | 12/2014 |

OTHER PUBLICATIONS

NINDS Autism Information Page. http://www.ninds.nih.gov/disorders/autism/autism.htm. 2015.*

American Academy of Neurology (2008). "Kids with Autism may have Gene that Causes Muscle Weakness," study conducted by John Shoffner, MD, owner of Medical Neurogenetics, LLC in Atlanta, GA and member of the American Academy of Neurology, to be presented at the American Academy of Neurology $60^{th}$ Anniversary Annual Meeting in Chicago on April 1219, 2008, press release on Apr. 13, 2008 located at <http://www.aan.com/PressRoom/Home/PressRelease/588>, last visited on Jul. 22, 2013, two pages.

Barbiroli, B. et al. (1995). "Lipoic (Thioctic) Acid Increases Brain Energy Availability and Skeletal Muscle Performance as Shown by In Vivo $^{31}$P'MRS in a Patient with Mitochondrial Cytopathy," *J. Neural.* 242(7):472-477.

Chariot, P. et al. (Apr. 1994). "Determination of the Blood Lactate:Pyruvate Ratio as a Noninvasive Test for the Diagnosis of Zidovudine Myopathy," *Arthritis & Rheumatism* 37(4):583-586.

Chariot, P. et al. (Jul. 1994). "Optimal Handling of Blood Samples for Routine Measurement of Lactate and Pyruvate," *Arch. Pathol. Lab. Med.* 118(7):695-697.

Chow, S.L. et al. (2005). "The Significance of Elevated CSF Lactate," *Arch. Dis. Child.* 90:1188-1189.

Chugani, D.C. et al. (May 1999). "Evidence of Altered Energy Metabolism in Autistic Children," *Progress in Neuro-Psychopharmacology & Biological Psychiatry* 23(4):635-641.

Coleman, M. et al. (Mar. 1985). "Autism and Lactic Acidosis," *Journal of Autism and Developmental Disorders* 15(1):1-8.

Erhola, M. et al. (1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," *FEBS Letters* 409(2):287-291.

Fabrizi, G.M. et al. (1996). "Autosomal Dominant Limb Girdle Myopathy with Ragged-Red Fibers and Cardiomyopathy. A Pedigree Study by In Vivo $^{31}$P'MR Spectroscopy Indicating a Multisystem Mitochondrial Defect," *Journal of the Neurological Sciences* 137(1):20-27.

Filipek, P.A. et al. (Dec. 2004). "Relative Carnitine Deficiency in Autism," *Journal of Autism and Developmental Disorders* 34(6):615-623.

Honda, M. et al. (2000). "Correlation of Urinary 8-Hydroxy-2'-Deoxyguanosine (8-OHdG), a Biomarker of Oxidative DNA Damage, and Clinical Features of Hematological Disorders: A Pilot Study," *Leukemia Research* 24(6):461-468.

Jauslin, M.L. et al. (2002). "A Cellular Model for Friedreich Ataxia Reveals Small-Molecule Glutathione Peroxidase Mimetics as Novel Treatment Strategy," *Human Molecular Genetics* 11(24):3055-3063.

Jauslin, M.L. et al. (2003, e-pub. Aug. 15, 2003). "Mitochondria-Targeted Antioxidants Protect Friedreich Ataxia Fibroblasts from Endogenous Oxidative Stress More Effectively Than Untargeted Antioxidants," *The FASEB Journal* 17(13):1972-1974.

Kaufmann, P. et al. (Apr. 27, 2004). "Cerebral Lactic Acidosis Correlates with Neurological Impairment in MELAS," *Neurology* 62(8):1297-1302.

Kim, J.Y. et al. (May 2004). "Urinary 8-Hydroxy-2'-Deoxyguanosine as a Biomarker of Oxidative DNA Damage in Workers Exposed to Fine Particulates," *Environmental Health Perspectives* 112(6):666-671.

Laszlo, A. et al. (1994). "Serum Serotonin, Lactate and Pyruvate Levels in Infantile Autistic Children," *Clinica Chimica Acta* 229:205-207.

Lynch, D.R. et al. (May 2002, e-pub. Feb. 25, 2002). "Near Infrared Muscle Spectroscopy in Patients with Friedreich's Ataxia," *Muscle Nerve* 25(5):664-673.

Matthews, P.M. et al. (Apr. 1991). "In Vivo Magnetic Resonance Spectroscopy of Brain and Muscle in a Type of Mitochondrial Encephalomyopathy (MERRF)," *Ann. Neurol.* 29(4):435438.

Medline Plus (Nov. 12, 2012). "Friedreich's Ataxia," updated by K. Sheth, MD, Department of Neurology, University of Maryland School of Medicine, Baltimore, MD, located at <http://www.nlm.nih.gov/medlineplus/ency/article/001411.htm>, last visited on Jul. 18, 2013, three pages.

Minami, N. et al. (1978). "Studies on Oxidation of Tocopherols. II. Oxidation Products of Tocopherol Model Compounds with Oxygen-Metal Complex," *Yakugaku Zasshi* 98(4):433-441.

Munnich, A. et al. (1992). "Clinical Aspects of Mitochondrial Disorders," *Journal of Inherited Metabolic Disease* 15(4):448-455.

Oliveira, G. et al. (2005). "Mitochondrial Dysfunction in Autism Spectrum Disorders: a Population-Based Study," *Developmental Medicine & Child Neurology* 47:185-189.

Pilger, A. et al. (2001). "Longitudinal Study of Urinary 8-Hydroxy-2'-Deoxyguanosine Excretion in Healthy Adults," *Free Radio. Res.* 35(3):273-280.

Pina, I.L. et al. (2003). "Exercise and Heart Failure: A Statement from the American Heart Association Committee on Exercise, Rehabilitation, and Prevention," *Circulation* 107:1210-1225.

(56) References Cited

OTHER PUBLICATIONS

Poling, J.S. et al. (Feb. 2006). "Developmental Regression and Mitochondrial Dysfunction in a Child with Autism," *J Child Neurol.* 21(2):170-172, five pages.

Rolfe, P. (2000). "In Vivo Near-Infrared Spectroscopy," *Annual Review of Biomedical Engineering* 2:715-754.

Rossignol, D.A. et al. (2008). "Evidence of Mitochondrial Dysfunction in Autism and Implications for Treatment," *American Journal of Biochemistry and Biotechnology* 4(2):208-217.

Strangman, G. et al. (2002). "Non-Invasive Neuroimaging Using Near-Infrared Light," *Biol. Psychiatry* 52:679-693.

Suarna, C. et al. (Oct. 1991). "Further Oxidation Products of 2,2,5,7,8-Pentamethyl-6-Chromanol," *Lipids* 26(10):847-852.

Taivassalo, T. et al. (2003). "The Spectrum of Exercise Tolerance in Mitochondrial Myopathies: A Study of 40 Patients," *Brain* 126:413-423.

Taivassalo, T. et al. (Jan. 2002, e-pub. Nov. 15, 2001). "Venous Oxygen Levels During Aerobic Forearm Exercise: An Index of Impaired Oxidative Metabolism in Mitochondrial Myopathy," *Ann. Neurol.* 51(1):38-44.

Ueda, K. et al. (Feb. 1997). "Evaluation of Changes in Hepatic Energy Metabolism During Exercise by Ketone Body Ratio in Humans," *J. Cardiol.* 29(2):95-102. (Translation of Abstract Only).

UMC-Cares (May 3, 2007). "Friedreich's Ataxia," previously located at <http://www.umc-cares.org/health_info/ADAM/Articles/001411.asp>, now located at <http://web.archive.org/web/20070503123643/<http://www.umc-cares.org/health_info/ADAM/Articles/001411.asp> last visited on Jul. 19, 2013, three pages.

Van Beekvelt, M.C.P. et al. (Oct. 1999). "Quantitative Near-Infrared Spectroscopy Discriminates Between Mitochondrial Myopathies and Normal Muscle," *Annals of Neurology* 46(4):667-670.

International Preliminary Report on Patentability mailed on Jul. 13, 2010, for PCT Patent Application No. PCT/US2009/030229, filed on Jan. 6, 2009, one page.

International Search Report mailed on Feb. 25, 2009, for PCT Patent Application No. PCT/US09/30229, filed on Jan. 6, 2009, two pages.

Written Opinion mailed on Feb. 25, 2009, for PCT Application No. PCT/US09/30229, filed on Jan. 6, 2009, five pages.

Smith et al., "Vitamin E. XLV. Synthesis of 2, 2, 7, 8-tetramethyl-5-benzyl-6-hydroxychroman and its behavior upon oxidation", 1944, J. of the American Chem. Soc. 66, pp. 1526-1531.

Zakharova et al., "Transformation products of vitamin E and its analog chroman C1 formed in the medium of oxidizing ethyl linoleate", 1992, Bioorganicheskaya Khimiya 18(7), pp. 985-995, CAPLUS.

Pfeffer G, Majamaa K, Turnbull DM, Thorburn D, Chinnery PF. Treatment for mitochondrial disorders. Cochrane Database Syst Rev. 2012, Issue 4. Art. No.: CD004426.DOI:10.1002/1451858. CD004426.pub.3.

\* cited by examiner

(HET)ARYL-P-QUINONE DERIVATIVES FOR TREATMENT OF MITOCHONDRIAL DISEASES

CROSS-REFERENCE TO RELATED APPLICATIONS

This application is a divisional of U.S. patent application Ser. No. 12/811,694, which is a U.S. National Phase Application of PCT/US2009/030229 having an International Filing Date of Jan. 6, 2009, which claims priority benefit of U.S. Provisional Patent Application No. 61/010,409 filed Jan. 8, 2008 and U.S. Provisional Patent Application No. 61/010,387 filed Jan. 8, 2008. All of those applications are hereby incorporated herein by reference in their entireties.

TECHNICAL FIELD

The application discloses compositions and methods useful for treatment, prevention, or suppression of diseases, developmental delays and symptoms related to mitochondrial disorders, such as Friedreich's ataxia, Leber's Hereditary Optic Neuropathy, Kearns-Sayre Syndrome, and mitochondrial myopathy, encephalopathy, lactacidosis, and stroke, cerebral vascular accidents, and for modulating energy biomarkers in a subject. Compositions of the present invention are administered to a subject for the purpose of compensating for mitochondrial dysfunction and for improving mitochondrial functions. Methods and compounds useful in treating other disorders such as amyotrophic lateral sclerosis (ALS), Huntington's, Parkinson's and pervasive development disorders are also disclosed.

BACKGROUND

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Krebs cycle), which generates reduced nicotinamide adenine dinucleotide (NADH+H$^+$) from oxidized nicotinamide adenine dinucleotide (NAD$^+$), and oxidative phosphorylation, during which NADH+H$^+$ is oxidized back to NAD$^+$. (The citric acid cycle also reduces flavin adenine dinucleotide, or FAD, to FADH$_2$; FADH$_2$ also participates in oxidative phosphorylation.)

The electrons released by oxidation of NADH+H$^+$ are shuttled down a series of protein complexes (Complex I, Complex II, Complex III, and Complex IV) known as the mitochondrial respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

One such disease is Friedreich's ataxia (FRDA or FA). Friedreich's ataxia is an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000-29,000 people (see www.nlm.nih.gov/medlineplus/ency/article/001411.htm) to 1 in 50,000 people (see www.umc-cares.org/health_info/ADAM/Articles/001411.asp). The disease causes the progressive loss of voluntary motor coordination (ataxia) and cardiac complications. Symptoms typically begin in childhood, and the disease progressively worsens as the patient grows older, patients eventually become wheelchair-bound due to motor disabilities.

Another disease linked to mitochondrial dysfunction is Leber's Hereditary Optic Neuropathy (LHON). The disease is characterized by blindness which occurs on average between 27 and 34 years of age; blindness can develop in both eyes simultaneously, or sequentially (one eye will develop blindness, followed by the other eye two months later on average). Other symptoms may also occur, such as cardiac abnormalities and neurological complications.

Yet another syndrome resulting from mitochondrial defects is mitochondrial myopathy, encephalopathy, lactacidosis, and stroke (MELAS). The disease can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke. Other severe complications, including neurological symptoms, are often present, and elevated levels of lactic acid in the blood occur.

Yet another syndrome resulting from a respiratory chain disorder is Myoclonus Epilepsy Associated with Ragged-Red Fibers (MERRF) syndrome, one of a group of rare muscular disorders that are called mitochondrial encephalomyopathies. Mitochondrial encephalomyopathies are disorders in which a defect in the genetic material arises from a part of the cell structure that releases energy (mitochondria). This can cause a dysfunction of the brain and muscles (encephalomyopathies). The mitochondrial defect as well as "ragged-red fibers" (an abnormality of tissue when viewed under a microscope) are always present. The most characteristic symptom of MERRF syndrome is myoclonic seizures that are usually sudden, brief, jerking, spasms that can affect the limbs or the entire body. Impairment of the ability to coordinate movements (ataxia), as well as an abnormal accumulation of lactic acid in the blood (lactic acidosis) may also be present in affected individuals. Difficulty speaking (dysarthria), optic atrophy, short stature, hearing loss, dementia, and involuntary jerking of the eyes (nystagmus) may also occur.

Yet another syndrome is Leigh's disease, a rare inherited neurometabolic disorder characterized by degeneration of the central nervous system. Leigh's disease can be caused by mutations in mitochondrial DNA or by deficiencies of pyruvate dehydrogenase. Symptoms of Leigh's disease usually begin between the ages of 3 months to 2 years and progress rapidly. In most children, the first signs may be poor sucking ability and loss of head control and motor skills. These symptoms may be accompanied by loss of appetite, vomiting, irritability, continuous crying, and seizures. As the disorder progresses, symptoms may also include generalized weakness, lack of muscle tone, and episodes of lactic acidosis, which can lead to impairment of respiratory and kidney function. Heart problems may also occur. In rare cases, Leigh's disease can begin during late adolescence or early adulthood and progress more slowly.

Yet another syndrome resulting from a respiratory chain disorder is Co-Enzyme Q10 Deficiency, the symptoms of which include encephalomyopathy, mental retardation, exercise intolerance, ragged-red fibers, and recurrent myoglobin in the urine.

Yet another syndrome resulting from a respiratory chain disorder is Complex I Deficiency or NADH dehydrogenase NADH-CoQ reductase deficiency, the symptoms of which are classified by three major forms: (1) fatal infantile multisystem disorder, characterized by developmental delay, muscle weakness, heart disease, congenital lactic acidosis, and respiratory failure; (2) myopathy beginning in childhood or in adult life, manifesting as exercise intolerance or weakness; and (3) mitochondrial encephalomyopathy (including MELAS), which may begin in childhood or adult life and consists of variable combinations of symptoms and signs, including ophthalmoplegia, seizures, dementia, ataxia, hearing loss, pigmentary retinopathy, sensory neuropathy, and uncontrollable movements.

Yet another syndrome resulting from a respiratory chain disorder is Complex II Deficiency or Succinate dehydrogenase deficiency, the symptoms of which include encephalomyopathy and various manifestations, including failure to thrive, developmental delay, hyoptonia, lethargy, respiratory failure, ataxia, myoclonus and lactic acidosis.

Yet another devastating syndrome resulting from a respiratory chain disorder is Complex II Deficiency or Ubiquinone-cytochrome C oxidoreductase deficiency, symptoms of which are categorized in four major forms: (1) fatal infantile encephalomyopathy, congenital lactic acidosis, hypotonia, dystrophic posturing, seizures, and coma; (2) encephalomyopathies of later onset (childhood to adult life): various combinations of weakness, short stature, ataxia, dementia, hearing loss, sensory neuropathy, pigmentary retinopathy, and pyramidal signs; (3) myopathy, with exercise intolerance evolving into fixed weakness; and (4) infantile histiocytoid cardiomyopathy.

Yet another syndrome resulting from a respiratory chain disorder is Complex IV Deficiency or cytochrome C oxidase deficiency, caused by a defect in Complex IV of the respiratory chain, the symptoms of which can be categorized in two major forms: (1) encephalomyopathy, which is typically normal for the first 6 to 12 months of life and then show developmental regression, ataxia, lactic acidosis, optic atrophy, ophthalmoplegia, nystagmus, dystonia, pyramidal signs, respiratory problems and frequent seizures; and (2) myopathy: Two main variants: (a) Fatal infantile myopathy: may begin soon after birth and accompanied by hypotonia, weakness, lactic acidosis, ragged-red fibers, respiratory failure, and kidney problems: and (b) Benign infantile myopathy: may begin soon after birth and accompanied by hypotonia, weakness, lactic acidosis, ragged-red fibers, respiratory problems, but (if the child survives) followed by spontaneous improvement.

Yet another syndrome resulting from a respiratory chain disorder is Complex V Deficiency or ATP synthase deficiency includes symptoms such as slow, progressive myopathy.

Yet another syndrome resulting from a respiratory chain disorder is CPEO or Chronic Progressive External Ophthalmoplegia Syndrome includes symptoms such as visual myopathy, retinitis pigmentosa, or dysfunction of the central nervous system.

Another mitochondrial disease is Kearns-Sayre Syndrome (KSS). KSS is characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis. Thus, KSS may affect many organ systems.

In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitoxic, neuronal injury, such as that associated with cerebral vascular accidents, seizures and ischemia.

Recent studies have suggested that as many 20 percent of patients with autism have markers for mitochondrial disease, (Shoffner, J. the 60$^{th}$ Annual American Academy of Neurology meeting in Chicago, Apr. 12-19, 2008; Poling, J S et al *J. Child Neurol.* 2008, 21(2) 170-2; and Rossignol et al., *Am. J. Biochem. & Biotech.* (2008) 4, 208-217.). Some cases of autism have been associated with several different organic conditions, including bioenergetic metabolism deficiency suggested by the detection of high lactate levels in some patients (Coleman M. et al, Autism and Lactic Acidosis, *J. Autism Dev. Disord.*, (1985) 15: 1-8; Laszlo et al Serum serotonin, lactate and pyruvate levels in infantile autistic children. *Clin. Chim. Acta* (1994) 229:205-207; and Chugani et al., Evidence of altered energy metabolism in autistic children, *Progr. Neuropsychopharmacol. Biol. Psychiat.*, (1999) 23:635-641) and by nuclear magnetic resonance imagining as well as positron emission tomography scanning which documented abnormalities in brain metabolism. Although the mechanism of hyperlactacidemia remains unknown, a likely possibility involves mitochondrial oxidative phosphorylation dysfunction in neuronal cells. A small subset of autistic patients diagnosed with deficiencies in complex I or III of the respiratory chain have been reported in the literature (see Oliveira, G., *Developmental Medicine & Child Neurology* (2005) 47 185-189; and Filipek, P A et al., *Journal of Autism and Developmental Disorders* (2004) 34:615-623.) However, in many of the cases of autism where there is some evidence of mitochondrial dysfunction, there is an absence of the classic features associated with mitochondrial disease, such as mitochondrial pathology in muscle biopsy (see Rossignol, D. A. et al., *Am J. Biochem. & Biotech,* (2008) 4 (2) 208-217).

The diseases above appear to be caused by defects in Complex I of the respiratory chain. Electron transfer from Complex I to the remainder of the respiratory chain is mediated by the compound coenzyme Q (also known as Ubiquinone). Oxidized coenzyme Q (CoQ$^{ox}$ or Ubiquinone) is reduced by Complex I to reduced coenzyme Q (CoQ$^{red}$ or Ubiquinol). The reduced coenzyme Q then transfers its electrons to Complex III of the respiratory chain (skipping over complex II), where it is re-oxidized to CoQ$^{ox}$ (Ubiquinone). CoQ$^{ox}$ can then participate in further iterations of electron transfer.

Very few treatments are available for patients suffering from these diseases. Recently, the compound Idebenone has been proposed for treatment of Friedreich's ataxia. While the clinical effects of Idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Pat. No. 7,179,928); clinical results for MitoQ have not yet been reported. For KSS, administration of coenzyme Q10 (CoQ10) and vitamin supplements, have shown only transient beneficial effects in individual cases.

1,4-Benzoquinones with aryl substitution have been described in international patent publication WO 2008/002641 as selective inhibitors of protein tyrosine phosphatases to treat neoplastic disorders, but this publication does not specifically disclose 2-(3-hydroxy-3-methylbutyl)-6-(het)aryl-p-quinone or 2-(3-hydroxy-3-methylbutyl)-3-(het)aryl-p-quinone derivatives, nor the use of the compounds of this invention for the treatment of mitochondrial diseases.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

In one embodiment, the invention embraces compounds of Formula I:

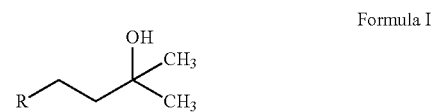

Formula I where,
R is selected from the group consisting of:

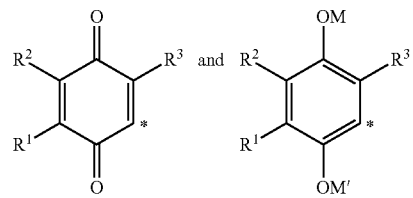

where the * indicates the point of attachment of R to the remainder of the molecule;
where M and M' are independently selected from hydrogen, —C(O)—R', —C(O)—($C_2$-$C_6$)-alkenyl, —C(O)—($C_2$-$C_6$)-alkynyl, —C(O)-aryl; —C(O)-heterocyclyl, —C(O)O—R', —C(O)NR'R", —SO$_2$OR', —SO$_2$—($C_1$-$C_6$)-alkyl, —SO$_2$—($C_1$-$C_6$)-haloalkyl, —SO$_2$-aryl, —SO$_2$—NR'R", —P(O)(OR')(OR"), and C-linked mono or di-peptide, where R' and R" are independently of each other hydrogen or ($C_1$-$C_6$)-alkyl optionally substituted with —OH, —NH$_2$, —NH($C_1$-$C_4$)-alkyl, —N(($C_1$-$C_4$)-alkyl)$_2$, —C(O)—OH, —C(O)—O—($C_1$-$C_4$)-alkyl or halogen;
where either
  $R^1$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl, hydroxy, ($C_1$-$C_6$)-alkoxy, CN, nitro, —COOR$^4$, —NR$^5$R$^6$, —CONR$^5$R$^6$, thiol, ($C_1$-$C_6$)-thioalkyl, and —COR$^4$; and wherein the ($C_0$-$C_6$)-alkyl group is optionally substituted with OH, —O($C_1$-$C_4$)-alkyl, —NH$_2$, —NH($C_1$-$C_4$)-alkyl, —N(($C_1$-$C_4$)-alkyl)$_2$, oxo or halogen; and $R^2$ and $R^3$ are independently selected from hydrogen, halogen, ($C_1$-$C_6$)-alkyl and ($C_1$-$C_6$)-alkoxy;
or
  $R^3$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl-, hydroxy, ($C_1$-$C_6$)-alkoxy, CN, nitro, —COOR$^4$, —NR$^5$R$^6$, —CONR$^5$R$^6$, thiol, ($C_1$-$C_6$)-thioalkyl-, and —COR$^4$; and wherein the ($C_0$-$C_6$)-alkyl group is optionally substituted with OH, —O($C_1$-

$C_4$)-alkyl, —$NH_2$, —$NH(C_1$-$C_4$)-alkyl, —$N((C_1$-$C_4$)-alkyl)$_2$, oxo or halogen; and $R^1$ and $R^2$ are independently selected from hydrogen, halogen, ($C_1$-$C_6$)-alkyl, and ($C_1$-$C_6$)-alkoxy;

where $R^4$ is hydrogen, ($C_1$-$C_6$)-alkyl, aryl, or aryl-($C_1$-$C_6$)-alkyl-; and where $R^5$ and $R^6$ are independently of each other hydroxy, ($C_1$-$C_6$)-alkoxy, ($C_1$-$C_6$)-alkyl, ($C_2$-$C_6$)-alkenyl, ($C_2$-$C_6$)-alkynyl, aryl, aryl-($C_1$-$C_4$)-alkyl-, heterocyclyl, or heterocyclyl-($C_1$-$C_6$)-alkyl-; wherein the alkyl, alkenyl, alkynyl, aryl and heterocyclyl groups can be further substituted with oxo, halogen, ($C_1$-$C_6$)-haloalkyl, hydroxy, ($C_1$-$C_6$)-alkoxy, or —$COOR^4$;

or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula I as described above.

In another embodiment the invention embraces compounds of Formula Ia of the following structure:

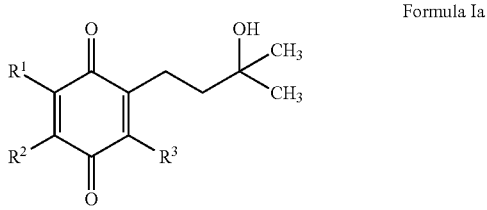

Formula Ia where either $R^1$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, thiol, ($C_1$-$C_6$)-thioalkyl, and —$COR^4$; and wherein the ($C_0$-$C_6$)-alkyl group is optionally substituted with OH, —$O(C_1$-$C_4$)-alkyl, —$NH_2$, —$NH(C_1$-$C_4$)-alkyl, —$N((C_1$-$C_4$)-alkyl)$_2$, oxo or halogen; and $R^2$ and $R^3$ are independently selected from hydrogen, halogen, ($C_1$-$C_6$)-alkyl and ($C_1$-$C_6$)-alkoxy;

or $R^3$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl-, hydroxy, ($C_1$-$C_6$)-alkoxy, CN, nitro, —$COOR^4$, —$NR^5R^6$, —$CONR^5R^6$, thiol, ($C_1$-$C_6$)-thioalkyl-, and —$COR^4$; and wherein the ($C_0$-$C_6$)-alkyl group is optionally substituted with OH, —$O(C_1$-$C_4$)-alkyl, —$NH_2$, —$NH(C_1$-$C_4$)-alkyl, —$N((C_1$-$C_4$)-alkyl)$_2$, oxo or halogen; and $R^1$ and $R^2$ are independently selected from hydrogen, halogen, ($C_1$-$C_6$)-alkyl, and ($C_1$-$C_6$)-alkoxy;

where $R^4$ is hydrogen, ($C_1$-$C_6$)-alkyl, aryl, or aryl-($C_1$-$C_6$)-alkyl-; and where $R^5$ and $R^6$ are independently of each other hydroxy, ($C_1$-$C_6$)-alkoxy, ($C_1$-$C_6$)-alkyl, ($C_2$-$C_6$)-alkenyl, ($C_2$-$C_6$)-alkynyl, aryl, aryl-($C_1$-$C_6$)-alkyl-, heterocyclyl, or heterocyclyl-($C_1$-$C_6$)-alkyl-; wherein the alkyl, alkenyl, alkynyl, aryl and heterocyclyl groups can be further substituted with oxo, halogen, ($C_1$-$C_6$)-haloalkyl, hydroxy, ($C_1$-$C_6$)-alkoxy, or —$COOR^4$;

or all salts, stereoisomers, mixtures of stereoisomers, prodrugs, metabolites, solvates, and hydrates thereof.

In another embodiment, the invention embraces compounds of Formula Ib:

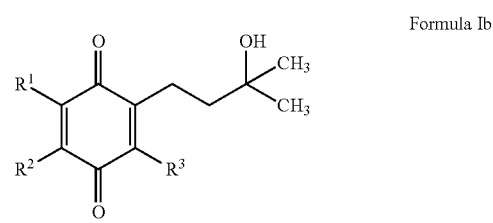

Formula Ib where, $R^1$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, thiol, ($C_1$-$C_6$)-thioalkyl, and —$COR^4$; and wherein the ($C_0$-$C_6$)-alkyl group is optionally substituted with OH, —$O(C_1$-$C_4$)-alkyl, —$NH_2$, —$NH(C_1$-$C_4$)-alkyl, —$N((C_1$-$C_4$)-alkyl)$_2$, oxo or halogen;

$R^2$ and $R^3$ are independently selected from hydrogen, halogen, ($C_1$-$C_6$)-alkyl, and ($C_1$-$C_6$)-alkoxy;

$R^4$ is hydrogen, ($C_1$-$C_6$)-alkyl, aryl, or aryl-($C_1$-$C_6$)-alkyl-; and $R^5$ and $R^6$ are independently of each other hydroxy, ($C_1$-$C_6$)-alkoxy, ($C_1$-$C_6$)-alkyl, ($C_2$-$C_6$)-alkenyl, ($C_2$-$C_6$)-alkynyl, aryl, aryl-($C_1$-$C_6$)-alkyl-, heterocyclyl, or heterocyclyl-($C_1$-$C_6$)-alkyl-; wherein the alkyl, alkenyl, alkynyl, aryl, and heterocyclyl groups can be further substituted with oxo, halogen, ($C_1$-$C_6$)-haloalkyl, hydroxy, ($C_1$-$C_6$)-alkoxy, or —$COOR^4$;

or all salts, stereoisomers, mixtures of stereoisomers, prodrugs, metabolites, solvates, and hydrates thereof.

In another embodiment, the invention embraces compounds of Formula Ib, where $R^2$ and $R^3$ are selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl; or all salts, stereoisomers, mixtures of stereoisomers, prodrugs, metabolites, solvates, and hydrates thereof.

In another embodiment, the invention embraces compounds of Formula Ib, where one of the $R^2$ and $R^{3'}$ groups is methyl, and the other group is hydrogen. In another embodiment the invention embraces compounds of Formula Ib, where $R^2$ and $R^3$ are methyl; or all salts, stereoisomers, mixtures of stereoisomers, prodrugs, metabolites, solvates, and hydrates thereof.

In another embodiment, the invention embraces compounds of Formula Ib, where one of the $R^2$ and $R^{3'}$ groups is methoxy; and in another embodiment $R^2$ and $R^{3'}$ groups are methoxy.

In another embodiment, the invention embraces compounds of Formula Ib, where one of $R^2$ and $R^3$ is halogen, in another embodiment $R^2$ and $R^3$ are halogen, in other embodiments $R^2$ and $R^{3'}$ are chloro, bromo, or fluoro.

In another embodiment, the invention embraces compounds of Formula Ib, where $R^1$ is aryl-($C_0$-$C_6$)-alkyl-, or all salts, stereoisomers, mixtures of stereoisomers, prodrugs, metabolites, solvates, and hydrates thereof. In another embodiment, the invention embraces compounds of Formula Ib, where $R^1$ is aryl, or all salts, stereoisomers, mixtures of stereoisomers, prodrugs, metabolites, solvates, and hydrates thereof. In another embodiment, the invention embraces compounds of Formula Ib, where $R^1$ is unsubstituted phenyl or naphthyl, or all salts, stereoisomers, mixtures of stereoisomers, prodrugs, metabolites, solvates, and hydrates thereof. In another embodiment, the invention embraces compounds of Formula Ib, where $R^1$ is phenyl or naphthyl substituted with ($C_1$-$C_6$)-alkyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, or —$COR^4$; or all salts, stereoisomers, mixtures of stereoisomers, prodrugs, metabolites, solvates, and hydrates thereof. In another embodiment, the invention embraces compounds of Formula Ib, where $R^1$ is phenyl substituted with one or more, for example one or two substituents selected from ($C_1$-$C_6$)-alkyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, and —$COR^4$; or all salts, stereoisomers, mixtures of stereoisomers, prodrugs, metabolites, solvates, and hydrates thereof. In another embodiment, the invention embraces compounds of Formula Ib, where $R^1$ is phenyl substituted with one or more substituents selected from ($C_1$-$C_6$)-alkyl, halogen, such as fluoro or chloro, and ($C_1$-$C_6$)-haloalkyl, such as $CF_3$, or $CHF_2$; or all salts, stereoisomers, mixtures of stereoisomers, prodrugs, metabolites, solvates, and hydrates thereof. In another embodiment, the invention embraces compounds of Formula Ib, where $R^1$ is aryl-($C_1$-$C_6$)alkyl-, optionally substituted with one or more substituents selected from ($C_1$-$C_6$)-alkyl, halogen, such as fluoro or chloro, and ($C_1$-$C_6$)-haloalkyl, such as $CF_$ or $CHF_2$; or all salts, stereoisomers, mixtures of stereoisomers, prodrugs, metabolites, solvates, and hydrates thereof. In another embodiment, the invention embraces compounds of Formula Ib, where $R^1$ is benzyl, phenylethyl, phenylpropyl, phenylbutyl, phenylpentyl, phenylhexyl, where the attachment of the phenyl to the alkyl chain can be at any open position and where the phenyl group is optionally substituted with one or more substituents selected from ($C_1$-$C_6$)-alkyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, and —$COR^4$; or all salts, stereoisomers, mixtures of stereoisomers, prodrugs, metabolites, solvates, and hydrates thereof.

In some embodiments, $R^1$ is phenyl mono-substituted with halogen, such as fluoro or chloro; and in other embodiments. $R^1$ is phenyl disubstituted with halogen such as fluoro or chloro. In another embodiment, $R^1$ is phenyl substituted with $CF_3$, or all salts, stereoisomers, mixtures of stereoisomers, prodrugs, metabolites, solvates, and hydrates thereof.

In some embodiments, $R^1$ is phenyl substituted with hydroxy or ($C_1$-$C_6$)-alkoxy; and in some other embodiments $R^1$ is phenyl substituted with methoxy, or all salts, stereoisomers, mixtures of stereoisomers, prodrugs, metabolites, solvates, and hydrates thereof.

In some embodiments, $R^1$ is phenyl substituted with CN; or all salts, stereoisomers, mixtures of stereoisomers, prodrugs, metabolites, solvates, and hydrates thereof.

In some embodiments, $R^1$ is unsubstituted benzyl or unsubstituted phenylpropyl; or all salts, stereoisomers, mixtures of stereoisomers, prodrugs, metabolites, solvates, and hydrates thereof.

In some embodiments, $R^1$ is phenyl-($C_{1-6}$)-alkyl-, where said alkyl group is substituted with OH, —$O(C_1$-$C_4)$-alkyl, —$NH_2$, —$NH(C_1$-$C_4)$-alkyl, —$N((C_1$-$C_4)$-alkyl$)_2$, oxo or halogen, for example the substituted alkyl group is 1-hydroxy-2-phenylethyl; or all salts, stereoisomers, mixtures of stereoisomers, prodrugs, metabolites, solvates, and hydrates thereof.

In some of the prior embodiments, the phenyl substitution is at the para position, in other embodiments the phenyl substitution is at the meta position, and in yet other embodiments the phenyl substitution is at the ortho position.

In another embodiment, the invention embraces compounds of Formula Ib, where $R^1$ is an unsubstituted heterocyclyl-($C_0$-$C_6$)-alkyl-, or all salts, stereoisomers, mixtures of stereoisomers, prodrugs, metabolites, solvates, and hydrates thereof. In another embodiment, the invention embraces compounds of Formula Ib, where $R^1$ is a substituted heterocyclyl-($C_0$-$C_6$)-alkyl-, or all salts, stereoisomers, mixtures of stereoisomers, prodrugs, metabolites, solvates, and hydrates thereof. In another embodiment, the invention embraces compounds of Formula Ib, where $R^1$ is an optionally substituted nitrogen containing heterocyclyl, for example imidazolyl, pyridinyl, pyrrolyl, and pyrimidinyl, or all salts, stereoisomers, mixtures of stereoisomers, prodrugs, metabolites, solvates, and hydrates thereof. In another embodiment, the invention embraces compounds of Formula Ib, where $R^1$ is an oxygen or sulfur containing heterocyclyl, for example tetrahydropyranyl, tetrahydrofuranyl, tetrahydrothienyl, pyranyl, furanyl, thienyl, benzopyranyl, or benzofuranyl, or all salts, stereoisomers, mixtures of stereoisomers, prodrugs, metabolites, solvates, and hydrates thereof.

In another embodiment, the invention embraces compounds of the Formula Ic:

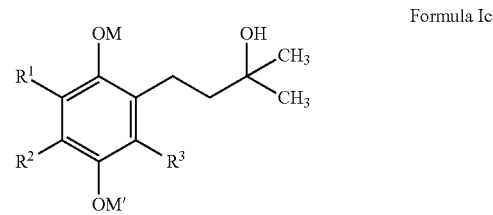

Formula Ic where,
$R^1$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl, hydroxy, ($C_1$-$C_6$)-alkoxy, CN, nitro, —$COOR^4$, —$NR^5R^6$, —$CONR^5R^6$, thiol, ($C_1$-$C_6$)-thioalkyl, and —$COR^4$; and wherein the ($C_0$-$C_6$)-alkyl group is optionally substituted with OH, —$O(C_1$-$C_6)$-alkyl, —$NH_2$, —$NH(C_1$-$C_4)$-alkyl, —$N((C_1$-$C_4)$-alkyl$)_2$, oxo or halogen;
$R^2$ and $R^3$ are independently selected from hydrogen, halogen, ($C_1$-$C_6$)-alkyl, and ($C_1$-$C_6$)-alkoxy;
$R^4$ is hydrogen, ($C_1$-$C_6$)-alkyl, aryl, or aryl-($C_1$-$C_6$)-alkyl-;
$R^5$ and $R^6$ are independently of each other hydroxy, ($C_1$-$C_6$)-alkoxy, ($C_1$-$C_6$)-alkyl, ($C_2$-$C_6$)-alkenyl, ($C_2$-$C_6$)-alkynyl, aryl, aryl-($C_1$-$C_6$)-alkyl-, heterocyclyl, or heterocyclyl-($C_1$-$C_6$)-alkyl-; wherein the alkyl, alkenyl, alkynyl, aryl and heterocyclyl groups can be further substituted with oxo, halogen, $(C_1-C_6)$-haloalkyl, hydroxy, $(C_1-C_6)$-alkoxy, or —COOR$^4$; and M and M' are independently selected from hydrogen, —C(O)—R', —C(O)—$(C_2-C_6)$-alkenyl, —C(O)—$(C_2-C_6)$-alkynyl, —C(O)-aryl, —C(O)-heterocyclyl, —C(O)O—R', —C(O)NR'R", —SO$_2$OR', —SO$_2$—$(C_1-C_6)$-alkyl, —SO$_2$—$(C_1-C_6)$-haloalkyl; —SO$_2$-aryl, —SO$_2$—NR'R", —P(O)(OR')(OR"), and C-linked mono- or di-peptide, where R' and R" are independently of each other hydrogen or $(C_1-C_6)$-alkyl optionally substituted with —OH, —NH$_2$, —NH($C_1-C_4$)alkyl, —N(($C_1-C_4$)alkyl)$_2$, —C(O)—OH, —C(O)—O—$(C_1-C_4)$-alkyl or halogen;

or all salts, stereoisomers, mixtures of stereoisomers, prodrugs, metabolites, solvates, and hydrates thereof.

In another embodiment, the invention embraces compounds of Formula Ic, where R$^2$ and R$^3$ are selected from methyl, ethyl, n-propyl, isopropyl, cyclopropyl, n-butyl, isobutyl, sec-butyl, i-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment and cyclohexyl; or all salts, stereoisomers, mixtures of stereoisomers, prodrugs, metabolites, solvates, and hydrates thereof.

In another embodiment, the invention embraces compounds of Formula Ic, where one of the R$^2$ and R$^3$ groups is methyl, and the remaining group is hydrogen. In another embodiment the invention embraces compounds of Formula Ic, where R$^2$ and R$^3$ are methyl; or all salts, stereoisomers, mixtures of stereoisomers, prodrugs, metabolites, solvates, and hydrates thereof.

In another embodiment, the invention embraces compounds of Formula Ic, where one of the R$^2$ and R$^{3'}$ groups is methoxy; and in another embodiment R$^2$ and R$^{3'}$ groups are methoxy.

In another embodiment, the invention embraces compounds of Formula Ic where one of R$^2$ and R$^3$ is halogen, in another embodiment R$^2$ and R$^3$ are halogen, in other embodiments R$^2$ and R$^{3'}$ are chloro, bromo, or fluoro.

In another embodiment, the invention embraces compounds of Formula Ic, where R$^1$ is aryl-$(C_0-C_6)$-alkyl-, or all salts, stereoisomers, mixtures of stereoisomers, prodrugs, metabolites, solvates, and hydrates thereof. In another embodiment, the invention embraces compounds of Formula Ic, where R$^1$ is aryl, or all salts, stereoisomers, mixtures of stereoisomers, prodrugs, metabolites, solvates, and hydrates thereof. In another embodiment, the invention embraces compounds of Formula Ic, where R$^1$ is unsubstituted phenyl or unsubstituted naphthyl, or all salts, stereoisomers, mixtures of stereoisomers, prodrugs, metabolites, solvates, and hydrates thereof. In another embodiment, the invention embraces compounds of Formula Ic, where R$^1$ is unsubstituted phenyl, or all salts, stereoisomers, mixtures of stereoisomers, prodrugs, metabolites, solvates, and hydrates thereof. In another embodiment, the invention embraces compounds of Formula Ic, where R$^1$ is phenyl or naphthyl substituted with one or more substituents selected from $(C_1-C_6)$-alkyl, halogen, $(C_1-C_6)$-haloalkyl, hydroxy, $(C_1-C_6)$-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof. In another embodiment, the invention embraces compounds of Formula Ic, where R$^1$ is phenyl substituted with one or two substituents selected from $(C_1-C_6)$-alkyl, halogen, $(C_1-C_6)$-haloalkyl, hydroxy, $(C_1-C_6)$-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof. In another embodiment, the invention embraces compounds of Formula Ic, where R$^1$ is phenyl substituted with one or more substituents selected from $(C_1-C_6)$-alkyl, halogen, such as fluoro or chloro, and $(C_1-C_6)$-haloalkyl, such as CF$_3$ or CHF$_2$; or all salts, stereoisomers, mixtures of stereoisomers, prodrugs, metabolites, solvates, and hydrates thereof. In another embodiment, the invention embraces compounds of Formula Ic, where R$^1$ is aryl-$(C_1-C_6)$-alkyl-, substituted with one or more substituents selected from $(C_1-C_6)$-alkyl, halogen, such as fluoro or chloro, and $(C_1-C_6)$-haloalkyl, such as CF$_3$ or CHF$_2$; or all salts, stereoisomers, mixtures of stereoisomers, prodrugs, metabolites, solvates, and hydrates thereof. In another embodiment, the invention embraces compounds of Formula Ic, where R$^1$ is benzyl, phenylethyl, phenylpropyl, phenylbutyl, phenylpentyl, phenylhexyl, where the attachment of the phenyl to the alkyl chain can be at any open position and where the phenyl group is substituted with one or more substituents selected from $(C_1-C_6)$-alkyl, halogen, $(C_1-C_6)$-haloalkyl, hydroxy, $(C_1-C_6)$-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof.

In some embodiments, R$^1$ is phenyl mono-substituted with halogen, such as fluoro or chloro, in other embodiments R$^1$ is phenyl disubstituted with halogen such as fluoro or chloro. In another embodiment R$^1$ is phenyl substituted with CF$_3$ or all salts, stereoisomers, mixtures of stereoisomers, prodrugs, metabolites, solvates, and hydrates thereof.

In some embodiments, R$^1$ is phenyl substituted with hydroxy or $(C_1-C_6)$-alkoxy; and in some other embodiments R$^1$ is phenyl substituted with methoxy, or all salts, stereoisomers, mixtures of stereoisomers, prodrugs, metabolites, solvates, and hydrates thereof.

In some embodiments, R$^1$ is phenyl substituted with CN; or all salts, stereoisomers, mixtures of stereoisomers, prodrugs, metabolites, solvates, and hydrates thereof.

In some embodiments, R$^1$ is unsubstituted benzyl or unsubstituted phenylpropyl; or all salts, stereoisomers, mixtures of stereoisomers, prodrugs, metabolites, solvates, and hydrates thereof.

In some of the prior embodiments, the phenyl substitution is at the para position, in other embodiments the phenyl substitution is at the meta position, and in yet other embodiments the phenyl substitution is at the ortho position.

In another embodiment, the invention embraces compounds of Formula Ic, where R$^1$ is an optionally substituted heterocyclyl-$(C_0-C_6)$-alkyl-, or all salts, stereoisomers, mixtures of stereoisomers, prodrugs, metabolites, solvates, and hydrates thereof. In another embodiment, the invention embraces compounds of Formula Ic, where R$^1$ is an optionally substituted heterocyclyl, or all salts, stereoisomers, mixtures of stereoisomers, prodrugs, metabolites, solvates, and hydrates thereof. In another embodiment, the invention embraces compounds of Formula Ic, where R$^1$ is a nitrogen containing heterocyclyl, for example imidazolyl, pyridinyl, pyrrolyl, and pyrimidinyl, or all salts, stereoisomers, mixtures of stereoisomers, prodrugs, metabolites, solvates, and hydrates thereof. In another embodiment, the invention embraces compounds of Formula Ic, where R$^1$ is an oxygen or sulfur containing heterocyclyl, for example tetrahydropyranyl, tetrahydrofuranyl, tetrahydrothienyl, pyranyl, furanyl, thienyl, benzodioxol, benzopyranyl, or benzofuranyl, or all salts, stereoisomers, mixtures of stereoisomers, prodrugs, metabolites, solvates, and hydrates thereof.

In another embodiment, the invention embraces compounds of Formula Ic, where M and M' are independently selected from hydrogen and —C(O)—R'; or all salts, stereoisomers, mixtures of stereoisomers, prodrugs, metabolites, solvates, and hydrates thereof. In another embodiment, the invention embraces compounds of Formula Ic, where M and M' are independently selected from hydrogen, —C(O)—H and —C(O)—($C_1$-$C_6$)-alkyl, for example M and M' are hydrogen or acetyl, or all salts, stereoisomers, mixtures of stereoisomers, prodrugs, metabolites, solvates, and hydrates thereof.

In another embodiment, the invention embraces compounds of Formula Ic, where $R^2$ and $R^3$ are methyl, and M and M' are hydrogen or acetyl, and a salt, a stereoisomer, or a mixture of stereoisomers. In another embodiment, the invention embraces compounds of Formula Ic, where $R^2$ and $R^3$ are methyl, $R^1$ is optionally substituted phenyl, and M and M' are independently hydrogen or acetyl, and a salt, a stereoisomer, or a mixture of stereoisomers. In another embodiment, the invention embraces compounds of Formula Ic, where $R^2$ and $R^3$ are methyl, $R^1$ is phenyl optionally substituted with one or more, for example one or two halogens, and M and M' are independently hydrogen or acetyl, and a salt, a stereoisomer, or a mixture of stereoisomers.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Ib or Formula Ic, where $R^2$ and $R^3$ are independently selected from ($C_1$-$C_4$) alkyl; and $R^1$ is optionally substituted phenyl; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Ib or Formula Ic, where $R^2$ and $R^3$ are methyl; and $R^1$ is phenyl substituted with one or more, for example one or two halogens; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Ic, where M and M' are independently selected from hydrogen and acetyl, $R^2$ and $R^3$ are independently selected from ($C_1$-$C_4$) alkyl; and $R^1$ is optionally substituted phenyl; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula Ic, where M and M' are independently selected from hydrogen and acetyl, $R^2$ and $R^3$ are independently selected from ($C_1$-$C_4$) alkyl; and $R^1$ is phenyl optionally substituted with halogens, or all salts, stereoisomers, mixtures of stereoisomers, prodrugs, metabolites, solvates, and hydrates thereof.

In another embodiment, the invention embraces compounds of Formula Id:

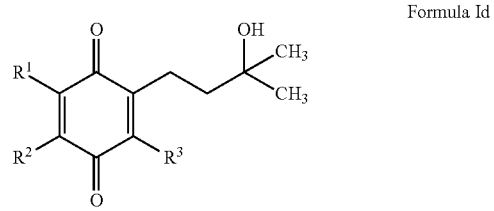

Formula Id where, $R^1$ and $R^2$ are independently selected from hydrogen, halogen, ($C_1$-$C_6$)-alkyl and ($C_1$-$C_6$)-alkoxy;

$R^3$ is aryl-($C_0$-$C_6$)-alkyl- or heterocyclyl-($C_0$-$C_6$)-alkyl-, wherein the aryl or heterocyclyl is optionally substituted with one or more substituents selected from ($C_1$-$C_6$)-alkyl, ($C_2$-$C_6$)-alkenyl, ($C_2$-$C_6$)-alkynyl, halogen, ($C_1$-$C_6$)-haloalkyl-, hydroxy, ($C_1$-$C_6$)-alkoxy, CN, nitro, —COO$R^4$, —N$R^5R^6$, —CON$R^5R^6$, thiol, ($C_1$-$C_6$)-thioalkyl-, and —CO$R^4$; and wherein the ($C_0$-$C_6$)-alkyl group is optionally substituted with OH, —O($C_1$-$C_4$)-alkyl, —N$H_2$, —NH($C_1$-$C_4$)-alkyl, —N(($C_1$-$C_4$)-alkyl)$_2$, oxo or halogen;

$R^4$ is hydrogen, ($C_1$-$C_6$)-alkyl, aryl, or aryl-($C_1$-$C_6$)-alkyl-; and $R^5$ and $R^6$ are independently of each other hydroxy, ($C_1$-$C_6$)-alkoxy, ($C_1$-$C_6$)-alkyl, ($C_2$-$C_6$)-alkenyl, ($C_2$-$C_6$)-alkynyl, aryl, aryl-($C_1$-$C_6$)-alkyl-, heterocyclyl, or heterocyclyl-($C_1$-$C_6$)-alkyl-; wherein the alkyl, alkenyl, alkynyl, aryl, and heterocyclyl groups can be further substituted with oxo, halogen, ($C_1$-$C_6$)-haloalkyl-, hydroxy, ($C_1$-$C_6$)-alkoxy, or —COO$R^4$;

or all salts, stereoisomers, mixtures of stereoisomers, prodrugs, metabolites, solvates, and hydrates thereof.

In another embodiment, the invention embraces compounds of Formula Id, where $R^1$ and $R^2$ are selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl; or all salts, stereoisomers, mixtures of stereoisomers, prodrugs, metabolites, solvates, and hydrates thereof.

In another embodiment, the invention embraces compounds of Formula Id, where one of the $R^1$ and $R^{2'}$ groups is methyl, and the other group is hydrogen. In another embodiment the invention embraces compounds of Formula Id, where $R^1$ and $R^2$ are methyl; or all salts, stereoisomers, mixtures of stereoisomers, prodrugs, metabolites, solvates, and hydrates thereof.

In another embodiment, the invention embraces compounds of Formula Id, where one of the $R^1$ and $R^{2'}$ groups is methoxy; and in another embodiment $R^1$ and $R^{2'}$ groups are methoxy.

In another embodiment, the invention embraces compounds of Formula Id, where one of $R^1$ and $R^2$ is halogen, in another embodiment $R^1$ and $R^2$ are halogen, in other embodiments $R^1$ and $R^2$ are chloro, bromo, or fluoro.

In another embodiment, the invention embraces compounds of Formula Id, where $R^3$ is aryl-$(C_0-C_6)$-alkyl-, or all salts, stereoisomers, mixtures of stereoisomers, prodrugs, metabolites, solvates, and hydrates thereof. In another embodiment, the invention embraces compounds of Formula Id, where $R^3$ is aryl, or all salts, stereoisomers, mixtures of stereoisomers, prodrugs, metabolites, solvates, and hydrates thereof. In another embodiment, the invention embraces compounds of Formula Id, where $R^3$ is unsubstituted phenyl or unsubstituted naphthyl, or all salts, stereoisomers, mixtures of stereoisomers, prodrugs, metabolites, solvates, and hydrates thereof. In another embodiment, the invention embraces compounds of Formula Id, where $R^3$ is phenyl or naphthyl substituted with $(C_1-C_6)$-alkyl, halogen, $(C_1-C_6)$-haloalkyl-, hydroxy, $(C_1-C_6)$-alkoxy, CN, nitro, —COOR$^4$, —NR$^5$R$^6$, —CONR$^5$R$^6$, or —COR$^4$; or all salts, stereoisomers, mixtures of stereoisomers, prodrugs, metabolites, solvates, and hydrates thereof. In another embodiment, the invention embraces compounds of Formula Id, where $R^3$ is phenyl substituted with one or more, for example one or two substituents selected from $(C_1-C_6)$-alkyl, halogen, $(C_1-C_6)$-haloalkyl-, hydroxy, $(C_1-C_6)$-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof. In another embodiment, the invention embraces compounds of Formula Id, where $R^3$ is phenyl substituted with one or more substituents selected from $C_1-C_6$-alkyl, halogen, such as fluoro or chloro, and $(C_1-C_6)$-haloalkyl-, such as $CF_3$ or $CHF_2$; or all salts, stereoisomers, mixtures of stereoisomers, prodrugs, metabolites, solvates, and hydrates thereof. In another embodiment, the invention embraces compounds of Formula Id, where $R^3$ is aryl-$(C_1-C_6)$ alkyl-, substituted with one or more substituents selected from $(C_1-C_6)$-alkyl, halogen, such as fluoro or chloro, and $(C_1-C_6)$-haloalkyl, such as $CF_3$ or $CHF_2$; or all salts, stereoisomers, mixtures of stereoisomers, prodrugs, metabolites, solvates, and hydrates thereof. In another embodiment, the invention embraces compounds of Formula Id, where $R^3$ is benzyl, phenylethyl, phenylpropyl, phenylbutyl, phenylpentyl, phenylhexyl, where the attachment of the phenyl to the alkyl chain can be at any open position and where the phenyl group is substituted with one or more substituents selected from $(C_1-C_6)$-alkyl, halogen, $(C_1-C_6)$-haloalkyl-, hydroxy, $(C_1-C_6)$-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof.

In some embodiments, $R^3$ is phenyl mono-substituted with halogen, such as fluoro or chloro; and in other embodiments. $R^3$ is phenyl disubstituted with halogen such as fluoro or chloro. In another embodiment $R^1$ is phenyl substituted with $CF_3$, or all salts, stereoisomers, mixtures of stereoisomers, prodrugs, metabolites, solvates, and hydrates thereof.

In some embodiments, $R^3$ is phenyl substituted with hydroxy or $(C_1-C_6)$-alkoxy; and in some other embodiments $R^3$ is phenyl substituted with methoxy, or all salts, stereoisomers, mixtures of stereoisomers, prodrugs, metabolites, solvates, and hydrates thereof.

In some embodiments, $R^3$ is phenyl substituted with CN; or all salts, stereoisomers, mixtures of stereoisomers, prodrugs, metabolites, solvates, and hydrates thereof.

In some embodiments, $R^3$ is unsubstituted benzyl, unsubstituted phenylethyl, or unsubstituted phenylpropyl; or all salts, stereoisomers, mixtures of stereoisomers, prodrugs, metabolites, solvates, and hydrates thereof.

In some embodiments, $R^3$ is phenyl-$(C_1-C_6)$alkyl, where said alkyl group is substituted with OH, —O$(C_1-C_4)$-alkyl, —NH$_2$, —NH$(C_1-C_4)$-alkyl, —N$((C_1-C_4)$-alkyl$)_2$, oxo or halogen, for example when the substituted alkyl group is 1-hydroxy-2-phenylethyl; or all salts, stereoisomers, mixtures of stereoisomers, prodrugs, metabolites, solvates, and hydrates thereof.

In some of the prior embodiments, the phenyl substitution is at the para position, in other embodiments the phenyl substitution is at the meta position, and in yet other embodiments the phenyl substitution is at the ortho position.

In another embodiment, the invention embraces compounds of Formula Id, where $R^3$ is an optionally substituted heterocyclyl-$(C_0-C_6)$-alkyl-, or all salts, stereoisomers, mixtures of stereoisomers, prodrugs, metabolites, solvates, and hydrates thereof. In another embodiment, the invention embraces compounds of Formula Id, where $R^3$ is an optionally substituted heterocyclyl, or all salts, stereoisomers, mixtures of stereoisomers, prodrugs, metabolites, solvates, and hydrates thereof. In another embodiment, the invention embraces compounds of Formula Id, where $R^3$ is an optionally substituted nitrogen containing heterocyclyl, for example imidazolyl, pyridinyl, pyrrolyl, and pyrimidinyl, or all salts, stereoisomers, mixtures of stereoisomers, prodrugs, metabolites, solvates, and hydrates thereof. In another embodiment, the invention embraces compounds of Formula Id, where $R^3$ is an oxygen or sulfur containing heterocyclyl, for example tetrahydropyranyl, tetrahydrofuranyl, tetrahydrothienyl, pyranyl, furanyl, thienyl, benzopyranyl, or benzofuranyl, or all salts, stereoisomers, mixtures of stereoisomers, prodrugs, metabolites, solvates, and hydrates thereof.

In another embodiment, the invention embraces compounds of the Formula Ie:

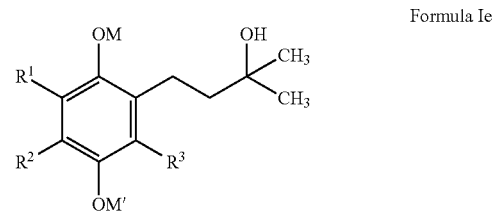

Formula Ie where, $R^1$ and $R^2$ are independently selected from hydrogen, halogen, $(C_1-C_6)$-alkyl, and $(C_1-C_6)$-alkoxy;

$R^3$ is aryl-$(C_0-C_6)$-alkyl- or heterocyclyl-$(C_0-C_6)$-alkyl-, wherein the aryl or heterocyclyl is optionally substituted with one or more substituents selected from $(C_1-C_6)$-alkyl, $(C_2-C_6)$-alkenyl, $(C_2-C_6)$-alkynyl, halogen, $(C_1-C_6)$-haloalkyl-, hydroxy, $(C_1-C_6)$-alkoxy, CN, nitro, —COOR$^4$, —NR$^5$R$^6$, —CONR$^5$R$^6$, thiol, $(C_1-C_6)$-thioalkyl-, and —COR$^4$; and wherein the $(C_0-C_6)$-alkyl group is optionally substituted with OH, —O$(C_1-C_4)$-alkyl, —NH$_2$, —NH$(C_1-C_4)$-alkyl, —N$((C_1-C_4)$-alkyl$)_2$, oxo or halogen;

$R^4$ is hydrogen, $(C_1-C_6)$-alkyl, aryl, or aryl-$(C_1-C_6)$-alkyl-;

$R^5$ and $R^6$ are independently of each other hydroxy, $(C_1-C_6)$-alkoxy, $(C_1-C_6)$-alkyl, $(C_2-C_6)$-alkenyl, $(C_2-C_6)$-alkynyl, aryl, aryl-$(C_1-C_6)$-alkyl-, heterocyclyl, or heterocyclyl-$(C_1-C_6)$-alkyl-; wherein the alkyl, alkenyl, alkynyl, aryl and heterocyclyl groups can be further substituted with oxo, halogen, $(C_1-C_6)$-haloalkyl-, hydroxy, $(C_1-C_6)$-alkoxy, or —COOR$^4$; and M and M' are independently selected from hydrogen, —C(O)—R', —C(O)—($C_2$-$C_6$)-alkenyl, —C(O)—($C_2$-$C_6$)-alkynyl, —C(O)-aryl; —C(O)-heterocyclyl, —C(O)O—R', —C(O)NR'R'', —SO$_2$OR', —SO$_2$—($C_1$-$C_6$)-alkyl, —SO$_2$—($C_1$-$C_6$)-haloalkyl, —SO$_2$-aryl, —SO$_2$—NR'R'', —P(O)(OR')(OR''), and C-linked mono or di-peptide, where R' and R'' are independently of each other hydrogen or ($C_1$-$C_6$)-alkyl optionally substituted with —OH, —NH$_2$, —NH($C_1$-$C_4$)alkyl, —N(($C_1$-$C_4$)alkyl)$_2$, —C(O)—OH, —C(O)—O—($C_1$-$C_4$)-alkyl or halogen;
or all salts, stereoisomers, mixtures of stereoisomers, prodrugs, metabolites, solvates, and hydrates thereof.

In another embodiment, the invention embraces compounds of Formula Ie, where $R^1$ and $R^2$ are selected from methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment and cyclohexyl; or all salts, stereoisomers, mixtures of stereoisomers, prodrugs, metabolites, solvates, and hydrates thereof.

In another embodiment, the invention embraces compounds of Formula Ie, where one of the $R^1$ and $R^2$ groups is methyl, and the remaining group is hydrogen. In another embodiment the invention embraces compounds of Formula Ie, where $R^1$ and $R^2$, are methyl; or all salts, stereoisomers, mixtures of stereoisomers, prodrugs, metabolites, solvates, and hydrates thereof.

In another embodiment, the invention embraces compounds of Formula Ie, where one of the $R^1$ and $R^{2'}$ groups is methoxy; and in another embodiment $R^1$ and $R^2$ groups are methoxy.

In another embodiment, the invention embraces compounds of Formula Ie, where one of $R^1$ and $R^2$ is halogen, in another embodiment $R^1$ and $R^2$ are halogen, in other embodiments $R^1$ and $R^{2'}$ are chloro, bromo, or fluoro.

In another embodiment, the invention embraces compounds of Formula Ie, where $R^3$ is aryl-($C_0$-$C_6$)-alkyl-, or all salts, stereoisomers, mixtures of stereoisomers, prodrugs, metabolites, solvates, and hydrates thereof. In another embodiment, the invention embraces compounds of Formula Ie, where $R^3$ is aryl, or all salts, stereoisomers, mixtures of stereoisomers, prodrugs, metabolites, solvates, and hydrates thereof. In another embodiment, the invention embraces compounds of Formula Ic, where $R^3$ is unsubstituted phenyl or unsubstituted naphthyl, or all salts, stereoisomers, mixtures of stereoisomers, prodrugs, metabolites, solvates, and hydrates thereof. In another embodiment, the invention embraces compounds of Formula Ie, where $R^3$ is unsubstituted phenyl, or all salts, stereoisomers, mixtures of stereoisomers, prodrugs, metabolites, solvates, and hydrates thereof. In another embodiment, the invention embraces compounds of Formula Ie, where $R^3$ is phenyl or naphthyl substituted with ($C_1$-$C_6$)-alkyl, halogen, ($C_1$-$C_6$)-haloalkyl-, hydroxy, ($C_1$-$C_6$)-alkoxy, CN, nitro, —COOR$^4$, —NR$^5$R$^6$, —CONR$^5$R$^6$, or —COR$^4$; or all salts, stereoisomers, mixtures of stereoisomers, prodrugs, metabolites, solvates, and hydrates thereof. In another embodiment, the invention embraces compounds of Formula Ie, where $R^3$ is phenyl substituted with one or more, for example one or two substituents selected from ($C_1$-$C_6$)-alkyl, halogen, ($C_1$-$C_6$)-haloalkyl-, hydroxy, ($C_1$-$C_6$)-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof. In another embodiment, the invention embraces compounds of Formula Ie, where $R^3$ is phenyl substituted with one or more substituents selected from ($C_1$-$C_6$)-alkyl, halogen, such as fluoro or chloro, and ($C_1$-$C_6$)-haloalkyl-, such as CF$_3$ or CHF$_2$; or all salts, stereoisomers, mixtures of stereoisomers, prodrugs, metabolites, solvates, and hydrates thereof. In another embodiment, the invention embraces compounds of Formula Ie, where $R^3$ is aryl-($C_1$-$C_6$)-alkyl-, substituted with one or more substituents selected from ($C_1$-$C_6$)-alkyl, halogen, such as fluoro or chloro, and ($C_1$-$C_6$)-haloalkyl-, such as CF$_3$ or CHF$_2$; or all salts, stereoisomers, mixtures of stereoisomers, prodrugs, metabolites, solvates, and hydrates thereof. In another embodiment, the invention embraces compounds of Formula Ie, where $R^3$ is benzyl, phenylethyl, phenylpropyl, phenylbutyl, phenylpentyl, phenylhexyl, where the attachment of the phenyl to the alkyl chain can be at any open position and where the phenyl group is substituted with one or more substituents selected from ($C_1$-$C_6$)-alkyl, halogen, ($C_1$-$C_6$)-haloalkyl-, hydroxy, ($C_1$-$C_6$)-alkoxy, CN, nitro, —COOR$^4$, —NR$^5$R$^6$, —CONR$^5$R$^6$, and —COR$^4$; or all salts, stereoisomers, mixtures of stereoisomers, prodrugs, metabolites, solvates, and hydrates thereof.

In some embodiments, $R^3$ is phenyl mono-substituted with halogen, such as fluoro or chloro, in other embodiments $R^3$ is phenyl disubstituted with halogen such as fluoro or chloro. In another embodiment $R^3$ is phenyl substituted with CF$_3$ or all salts, stereoisomers, mixtures of stereoisomers, prodrugs, metabolites, solvates, and hydrates thereof.

In some embodiments, $R^3$ is phenyl substituted with hydroxy or ($C_1$-$C_6$)-alkoxy; and in some other embodiments $R^3$ is phenyl substituted with methoxy, or all salts, stereoisomers, mixtures of stereoisomers, prodrugs, metabolites, solvates, and hydrates thereof.

In some embodiments, $R^3$ is phenyl substituted with CN; or all salts, stereoisomers, mixtures of stereoisomers, prodrugs, metabolites, solvates, and hydrates thereof.

In some embodiments, $R^3$ is phenyl-($C_1$-$C_6$)-alkyl-, or all salts, stereoisomers, mixtures of stereoisomers, prodrugs, metabolites, solvates, and hydrates thereof. In some embodiments, $R^1$ is unsubstituted benzyl or unsubstituted phenylpropyl; or all salts, stereoisomers, mixtures of stereoisomers, prodrugs, metabolites, solvates, and hydrates thereof.

In some embodiments, $R^3$ is unsubstituted benzyl or unsubstituted phenylpropyl; or all salts, stereoisomers, mixtures of stereoisomers, prodrugs, metabolites, solvates, and hydrates thereof.

In some of the prior embodiments, the phenyl substitution is at the para position, and in other embodiments the phenyl substitution is at the meta position and in yet other embodiments the phenyl substitution is at the ortho position.

In another embodiment, the invention embraces compounds of Formula Ie, where $R^3$ is heterocyclyl-($C_0$-$C_6$)-alkyl-, or all salts, stereoisomers, mixtures of stereoisomers, prodrugs, metabolites, solvates, and hydrates thereof. In another embodiment, the invention embraces compounds of Formula Ie, where $R^3$ is an optionally substituted heterocyclyl, or all salts, stereoisomers, mixtures of stereoisomers, prodrugs, metabolites, solvates, and hydrates thereof. In another embodiment, the invention embraces compounds of Formula Ie, where $R^3$ is a nitrogen containing heterocyclyl, for example imidazolyl, pyrazolyl, pyridinyl, pyrrolyl, pyrimidinyl, pyridazinyl, indolyl, thiazolyl, or oxazolyl, or all salts, stereoisomers, mixtures of stereoisomers, prodrugs, metabolites, solvates, and hydrates thereof. In another embodiment, the invention embraces compounds of Formula Ie, where $R^3$ is an oxygen or sulfur containing heterocyclyl, for example tetrahydropyranyl, tetrahydrofuranyl, tetrahydrothienyl, pyranyl, furanyl, thienyl, benzodioxol, benzopyranyl, or benzofuranyl, or all salts, stereoisomers, mixtures of stereoisomers, prodrugs, metabolites, solvates, and hydrates thereof.

In another embodiment, the invention embraces compounds of Formula Ic, where M and M' are independently selected from hydrogen, and —C(O)—R'; or all salts, stereoisomers, mixtures of stereoisomers, prodrugs, metabolites, solvates, and hydrates thereof. In another embodiment, the invention embraces compounds of Formula Ie, where M and M' are independently selected from hydrogen, —C(O)—H and —C(O)—($C_1$-$C_6$)-alkyl, for example M and M' are independently selected from hydrogen and acetyl, or all salts, stereoisomers, mixtures of stereoisomers, prodrugs, metabolites, solvates, and hydrates thereof.

In another embodiment, the invention embraces compounds of Formula Ie, where $R^1$ and $R^2$ are methyl, and M and M' are independently selected from hydrogen and acetyl, and a salt, a stereoisomer, or a mixture of stereoisomers. In another embodiment, the invention embraces compounds of Formula Ie, where $R^1$ and $R^2$ are methyl, $R^3$ is optionally substituted phenyl, and M and M' are independently selected from hydrogen and acetyl, and a salt, a stereoisomer, or a mixture of stereoisomers. In another embodiment, the invention embraces compounds of Formula Ie, where $R^1$ and $R^2$ are methyl, $R^3$ is phenyl optionally substituted with one or more, for example one or two halogens, and M and M' are independently selected from hydrogen and acetyl, and a salt, a stereoisomer, or a mixture of stereoisomers.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Id or Formula Ie, where $R^1$ and $R^2$ are independently selected from ($C_1$-$C_4$) alkyl; and R is optionally substituted phenyl; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Id or Formula Ie, where $R^1$ and $R^2$ are independently selected from ($C_1$-$C_4$) alkyl; and $R^1$ is phenyl substituted with one or more, for example one or two halogens; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula Ie, where M and M' are independently selected from hydrogen and acetyl, $R^1$ and $R^2$ are independently selected from ($C_1$-$C_4$) alkyl; and $R^3$ is optionally substituted phenyl; or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds of Formula Ie, where M and M' are independently selected from hydrogen and acetyl, $R^1$ and $R^2$ are independently selected from ($C_1$-$C_4$) alkyl; and $R^3$ is phenyl optionally substituted with halogens, or all salts, stereoisomers, mixtures of stereoisomers, prodrugs, metabolites, solvates, and hydrates thereof.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount of one or more compounds of Formula I, Formula Ia, Formula Ib, Formula Ic, Formula Id or Formula Ie; or all salts, stereoisomers, mixtures of stereoisomers, prodrugs, metabolites, solvates, and hydrates thereof.

In another embodiment, the invention embraces compounds of Formula I, selected from:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
4-(5-(3-hydroxy-3-methylbutyl)-2,4-dimethyl-3,6-dioxocyclohexa-1,4-dienyl)benzonitrile;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione;
2-(4-fluorophenyl)-6-(3-hydroxy-3-methylbutyl)-3,5-dimethylcyclohexa-2,5-diene-1,4-dione;
2-(4-chlorophenyl)-6-(3-hydroxy-3-methylbutyl)-3,5-dimethylcyclohexa-2,5-diene-1,4-dione; and
2-(2,3-dihydrobenzofuran-2-yl)-6-(3-hydroxy-3-methylbutyl)-3,5-dimethylcyclohexa-2,5-diene-1,4-dione;
2-(3-hydroxy-3-methylbutyl)-5,6-dimethyl-3-phenethylcyclohexa-2,5-diene-1,4-dione;
2-(3-hydroxy-3-methylbutyl)-5,6-dimethyl-3-phenylcyclohexa-2,5-diene-1,4-dione;
2-benzyl-3-(3-hydroxy-3-methylbutyl)-5,6-dimethylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(1-hydroxy-2-phenylethyl)-3-(3-hydroxy-3-methylbutyl)-5,6-dimethylcyclohexa-2,5-diene-1,4-dione;
2-(3-hydroxy-3-methylbutyl)-3-(4-methoxyphenyl)-5,6-dimethyl-cyclohexa-2,5-diene-1,4-dione;
2-(3-hydroxy-3-methylbutyl)-5,6-dimethyl-3-(4-(trifluoromethyl)-phenyl)cyclohexa-2,5-diene-1,4-dione;
2-(3-hydroxy-3-methylbutyl)-5,6-dimethyl-3-(naphthalen-2-yl)cyclohexa-2,5-diene-1,4-dione;
2-(benzofuran-2-yl)-3-(3-hydroxy-3-methylbutyl)-5,6-dimethylcyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethyl phenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2,5-diene-1,4-dione;
2-(4-tert-butylphenyl)-3-(3-hydroxy-3-methylbutyl)-5,6-dimethyl-cyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;

4-(2-(3-hydroxy-3-methylbutyl)-4,5-dimethyl-3,6-dioxocyclohexa-1,4-dienyl)benzonitrile;
2-(3,4-difluorophenyl)-3-(3-hydroxy-3-methylbutyl)-5,6-dimethyl-cyclohexa-2,5-diene-1,4-dione;
2-(2-fluorophenyl)-3-(3-hydroxy-3-methylbutyl)-5,6-dimethylcyclohexa-2,5-diene-1,4-dione;
2-(3-hydroxy-3-methylbutyl)-3-(3-methoxyphenyl)-5,6-dimethyl-cyclohexa-2,5-diene-1,4-dione;
2-(4-fluoro-2-methoxyphenyl)-3-(3-hydroxy-3-methylbutyl)-5,6-dimethylcyclohexa-2,5-diene-1,4-dione;
2-(benzo[d][1,3]dioxol-5-yl)-3-(3-hydroxy-3-methylbutyl)-5,6-dimethylcyclohexa-2,5-diene-1,4-dione;
2-(2,4-difluorophenyl)-3-(3-hydroxy-3-methylbutyl)-5,6-dimethylcyclohexa-2,5-diene-1,4-dione;
2-(3-hydroxy-3-methylbutyl)-3-(4-methoxyphenyl)-5,6-dimethylcyclohexa-2,5-diene-1,4-dione;
2-(3,5-bis(trifluoromethyl)phenyl)-3-(3-hydroxy-3-methylbutyl)-5,6-dimethylcyclohexa-2,5-diene-1,4-dione; and
2-(4-chlorophenyl)-6-(3-hydroxy-3-methylbutyl)-3,5-dimethylcyclohexa-2,5-diene-1,4-dione;
or all salts, stereoisomers, mixtures of stereoisomers, prodrugs, metabolites, solvates, and hydrates thereof.

In another embodiment, the invention embraces compounds of Formula I, selected from:
2-(3-hydroxy-3-methylbutyl)-5,6-dimethyl-3-(2-(thiazol-2-yl)ethyl)cyclohexa-2,5-diene-1,4-dione;
2-(3-hydroxy-3-methylbutyl)-5,6-dimethyl-3-(2-(thiazol-5-yl)ethyl)cyclohexa-2,5-diene-1,4-dione;
2-(3-hydroxy-3-methylbutyl)-5,6-dimethyl-3-(2-(pyridin-2-yl)ethyl)cyclohexa-2,5-diene-1,4-dione;
2-(3-hydroxy-3-methylbutyl)-5,6-dimethyl-3-(2-(pyridazin-4-yl)ethyl)cyclohexa-2,5-diene-1,4-dione;
2-(3-hydroxy-3-methylbutyl)-5,6-dimethyl-3-(2-(thiophen-2-yl)ethyl)cyclohexa-2,5-diene-1,4-dione;
2-(3-hydroxy-3-methylbutyl)-5,6-dimethyl-3-(2-(thiophen-3-yl)ethyl)cyclohexa-2,5-diene-1,4-dione;
2-(2-(furan-2-yl)ethyl)-3-(3-hydroxy-3-methylbutyl)-5,6-dimethylcyclohexa-2,5-diene-1,4-dione;
2-(2-(furan-3-yl)ethyl)-3-(3-hydroxy-3-methylbutyl)-5,6-dimethylcyclohexa-2,5-diene-1,4-dione;
2-(2-(1H-pyrazol-5-yl)ethyl)-3-(3-hydroxy-3-methylbutyl)-5,6-dimethylcyclohexa-2,5-diene-1,4-dione;
2-(2-(1H-pyrazol-4-yl)ethyl)-3-(3-hydroxy-3-methylbutyl)-5,6-dimethylcyclohexa-2,5-diene-1,4-dione;
2-(2-(1H-pyrazol-1-yl)ethyl)-3-(3-hydroxy-3-methylbutyl)-5,6-dimethylcyclohexa-2,5-diene-1,4-dione;
2-(2-(1H-imidazol-5-yl)ethyl)-3-(3-hydroxy-3-methylbutyl)-5,6-dimethylcyclohexa-2,5-diene-1,4-dione;
2-(2-(1H-imidazol-2-yl)ethyl)-3-(3-hydroxy-3-methylbutyl)-5,6-dimethylcyclohexa-2,5-diene-1,4-dione;
2-(3-hydroxy-3-methylbutyl)-5,6-dimethyl-3-(2-(oxazol-5-yl)ethyl)cyclohexa-2,5-diene-1,4-dione;
2-(3-hydroxy-3-methylbutyl)-5,6-dimethyl-3-(2-(oxazol-2-yl)ethyl)cyclohexa-2,5-diene-1,4-dione;
2-(3-hydroxy-3-methylbutyl)-5,6-dimethyl-3-(2-(oxazol-4-yl)ethyl)cyclohexa-2,5-diene-1,4-dione; and
2-(2-(1H-indol-3-yl)ethyl)-3-(3-hydroxy-3-methylbutyl)-5,6-dimethylcyclohexa-2,5-diene-1,4-dione;
or all salts, stereoisomers, mixtures of stereoisomers, prodrugs, metabolites, solvates, and hydrates thereof.

In other embodiments, including any of the foregoing embodiments, the mitochondrial disorder is selected from the group consisting of mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); chronic progressive external ophthalmoplegia (CPEO); Leigh Disease; Kearns-Sayre Syndrome (KSS); Friedreich's Ataxia (FA); Co-Enzyme Q10 Deficiency; Complex I Deficiency; Complex II Deficiency; Complex III Deficiency; Complex IV Deficiency; Complex V Deficiency; other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age-associated diseases; cerebral vascular diseases; macular degeneration; diabetes; pervasive development disorders, such as autistic disorder (ASD), Asperger's disorder, childhood disintegrative disorder (CDD), Rett's disorder, and PDD-Not Otherwise Specified (PDD-NOS); and cancer.

In another embodiment, including any of the foregoing embodiments, the mitochondrial disorder is a mitochondrial respiratory chain disorder. In a particular embodiment, the mitochondrial respiratory chain disorder is a respiratory protein chain disorder.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, and Stroke (MELAS); Leber's Hereditary Optic Neuropathy (LHON); chronic progressive external ophthalmoplegia (CPEO); Leigh Disease; Kearns-Sayre Syndrome (KSS); and Friedreich's Ataxia (FA).

In another embodiment of the invention, including any of the foregoing embodiments, the mitochondrial disorder is Friedreich's ataxia (FRDA). In another embodiment of the invention, the mitochondrial disorder is Leber's Hereditary Optic Neuropathy (LHON). In another embodiment of the invention, including any of the foregoing embodiments, the mitochondrial disorder is mitochondrial myopathy, encephalopathy, lactacidosis, and stroke (MELAS). In another embodiment of the invention, including any of the foregoing embodiments, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, including any of the foregoing embodiments, the mitochondrial disorder is Parkinson's disease. In another embodiment of the invention, including any of the foregoing embodiments, the mitochondrial disorder is Huntington's disease. In another embodiment of the invention, including any of the foregoing embodiments, the mitochondrial disorder is amyotrophic lateral sclerosis disease. In another embodiment, the disorder is cerebral vascular accidents. In another embodiment, the disorder is Pervasive Developmental Disorder PDD, including Autistic Disorder (ASD), Asperger's Disorder, Childhood Disintegrative Disorder (CDD), Rett's Disorder, and PDD-Not Otherwise Specified (PDD-NOS), and in a particular embodiment, the disorder is autism.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels. NADH (NADH+H$^+$)

or NADPH (NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing a mitochondrial disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; and other subjects with acute, chronic, or ongoing energy demands who can benefit from enhancement of energy biomarkers.

In another embodiment, the invention embraces one or more compounds of Formula I, Formula Ia, Formula Ib, Formula Ic, Formula Id and/or Formula Ie, in combination with a pharmaceutically acceptable excipient, carrier, or vehicle.

In another embodiment, the invention embraces the use of one or more compounds of Formula I, Formula Ia, Formula Ib, Formula Ic, Formula Id and/or Formula Ie, in the therapy of mitochondrial disease. In another embodiment, the invention embraces the use of one or more compounds of Formula I, Formula Ia, Formula Ib, Formula Ic, Formula Id and/or Formula Ie, in the manufacture of a medicament for use in therapy of mitochondrial disease.

For the purpose of the invention, the compounds of Formula I, Formula Ia, Formula Ib, Formula Ic, Formula Id and/or Formula Ie include derivatives thereof wherein one or more hydrogen atoms has been replaced by a hydrogen isotope, for example by deuterium. For the purpose of the invention, the compounds of Formula I, Formula Ia, Formula Ib, Formula Ic, Formula Id and/or Formula Ie include crystalline form, and non-crystalline forms thereof.

For all of the compounds and methods described above, the quinone form can also be used in its reduced (hydroquinone) form when desired. Likewise, the hydroquinone form can also be used in its oxidized (quinone) form when desired.

MODES FOR CARRYING OUT THE INVENTION

The invention embraces compounds useful in treating or suppressing mitochondrial disorders, and methods of using such compounds for modulation of energy biomarkers. The redox active therapeutics for treatment or suppression of mitochondrial diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

By "respiratory chain disorder" is meant a disorder which results in the decreased utilization of oxygen by a mitochondrion, cell, tissue, or individual, due to a defect or disorder in a protein contained in the mitochondrial respiratory chain. By "respiratory chain" is meant the components (including, but not limited to, proteins, tetrapyrroles, and cytochromes) comprising mitochondrial complex I, II, III, IV, and/or V; "respiratory chain protein" refers to the protein components of those complexes.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes all stereoisomers of the compounds, including diasteromers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York:

Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.). Washington: The Academy, 1977.

Metabolites of the compounds are also embraced by the invention.

"$(C_1-C_6)$-alkyl" is intended to embrace a saturated linear, branched, cyclic, or a combination of linear and/or branched and/or cyclic hydrocarbon chain and/or ring of 1 to 6 carbon atoms. Examples of "$(C_1-C_6)$-alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl fragment, cyclopentyl, hexyl where the point of attachment of the hexyl group to the remainder of the molecule can be at any location on the hexyl fragment, and cyclohexyl. This term includes mono and divalent hydrocarbon chains, i.e. $(C_1-C_6)$-alkyl and $(C_1-C_6)$-alkylene chains of 1 to 6 carbon atoms.

"$(C_0-C_6)$-alkyl" is intended to embrace a saturated linear, branched, cyclic, or a combination of linear and/or branched and/or cyclic hydrocarbon chain and/or ring of 1 to 6 carbon atoms, as described above for $(C_1-C_6)$-alkyl, or where the alkyl group is absent. This term includes mono and divalent hydrocarbon chains, i.e. $(C_1-C_6)$-alkyl and $(C_1-C_6)$-alkylene chains of 1 to 6 carbon atoms.

"Halogen" or "halo" designates fluoro (—F), chloro (—Cl), bromo (—Br), and iodo (—I).

"$(C_1-C_6)$-haloalkyl" is intended to embrace any $(C_1-C_6)$-alkyl substituent having at least one halogen substituent; the halogen can be attached via any valence on the $(C_1-C_6)$-alkyl group. One subset of $(C_1-C_6)$-haloalkyl is —$CF_3$, —$CCl_3$, —$CBr_3$, and —$CI_3$. Another subset of $(C_1-C_6)$-haloalkyl is —$CHF_2$, —$CHCl_2$, —$CHBr_2$, and —$CHI_2$. Another subset of $(C_1-C_6)$-haloalkyl is —$CH_2F$, —$CH_2Cl$, —$CH_2Br$, and —$CH_2I$. Another subset of $(C_1-C_6)$-haloalkyl is the subset of $(C_1-C_6)$-perhaloalkyls where all available valences are replaced by halogens. Another subset of $(C_1-C_6)$-haloalkyl is the subset of $(C_1-C_6)$-perfluoroalkyl; where all available valences are replaced by fluorines. Another subset of $(C_1-C_6)$-haloalkyl is the subset of $(C_1-C_6)$-perchloroalkyl; that is, $(C_1-C_6)$-alkyl with all available valences replaced by chlorines.

The term "aryl" is intended to embrace an aromatic cyclic hydrocarbon group of from 6 to 20 carbon atoms having a single ring (e.g., phenyl) or multiple condensed (fused) rings (e.g., naphthyl or anthryl).

The term "Friedreich's ataxia" is intended to embrace other ataxias, and is also sometimes referred to as hereditary ataxia, familiar ataxia, or Friedreich's tabes.

The terms "heterocycle", "heterocyclic", "heterocyclo", and "heterocyclyl" is intended to encompass a monovalent, saturated, partially unsaturated, or unsaturated (heteroaryl) carbocyclic radical having one or more rings incorporating one, two, three or four heteroatoms within the ring (chosen from nitrogen, oxygen, and/or sulfur). Examples of heterocycles include morpholine, piperidine, piperazine, thiazolidine, pyrazolidine, pyrazoline, imidazolidine, pyrrolidine, tetrahydropyran, tetrahydrofuran, quinuclidine, pyridine, pyrazine, imidazoline, thiazole, isothiazole, pyrazine, triazine, pyrimidine, pyridazine, pyrazole, thiophene, pyrrole, pyran, furan, indole, quinoline, quinazoline, benzodioxole, benzimidazole, benzothiophene, benzofuran, benzoxazole, benzothiazole, benzotriazole, imidazo-pyridines, pyrazolopyridines, pyrazolo-pyrazine, acridine, carbazole, and the like.

The terms "Parkinson's", (also called "Parkinsonism" and "Parkinsonian syndrome") ("PD") is intended to include not only Parkinson's disease but also drug-induced Parkinsonism and post-encephalitic Parkinsonism. Parkinson's disease is also known as paralysis agitans or shaking palsy. It is characterized by tremor, muscular rigidity and loss of postural reflexes. The disease usually progresses slowly with intervals of 10 to 20 years elapsing before the symptoms cause incapacity. Due to their mimicry of effects of Parkinson's disease, treatment of animals with methamphetamine or MPTP has been used to generate models for Parkinson's disease. These animal models have been used to evaluate the efficacy of various therapies for Parkinson's disease.

The term "Pervasive Developmental Disorder" (PDD) is intended to include neurological disorders characterized by severe and pervasive impairment in several areas of development, including social interaction and communications skills. The five disorders under PDD are Autistic Disorder, Asperger's Disorder, Childhood Disintegrative Disorder (CDD), Rett's Disorder, and PDD-Not Otherwise Specified (PDD-NOS). Specific diagnostic criteria for each of these disorders can be found in the Diagnostic & Statistical Manual of Mental Disorders (DSM-IV-TR) as distributed by the American Psychiatric Association (APA). Autistic Spectrum Disorder (ASD) is an umbrella term that is used to represent a broad heterogeneous disorder by collectively grouping autistic disorder, Asperger's Disorder and PDD-NOS.

In general, the nomenclature used in this Application was generated with the help of naming package within the ChemOffice® version 11.0 suite of programs by CambridgeSoft Corp (Cambridge, Mass.).

Diseases Amenable to Treatment or Suppression with Compounds and Methods of the Invention A variety of diseases are believed to be caused or aggravated by mitochondrial disorders and impaired energy processing, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FA), other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; and certain age-associated diseases, particularly diseases for which CoQ10 has been proposed for treatment, such as macular degeneration, diabetes, and cancer. Mitochondrial dysfunction is also implicated in excitotoxic, neuronal injury, such as that associated with seizures and ischemia. Mitochondrial dysfunction is also implicated in pervasive development disorders such as autistic syndrome disorder (ASD), Asperger's disorder, childhood sisintegrative sisorder (CDD), Rett's sisorder, and PDD-Not Otherwise Specified (PDD-NOS).

Clinical Assessment of Mitochondrial Dysfunction and Efficacy of Therapy

Several readily measurable clinical markers are used to assess the metabolic state of patients with mitochondrial disorders. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH ($NADH+H^+$) or NADPH ($NADPH+H^+$) levels; NAD or NADP levels; ATP levels; anaerobic threshold; reduced coenzyme Q ($CoQ^{red}$) levels; oxidized coenzyme Q ($CoQ^{ox}$) levels; total coenzyme Q ($CoQ^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies ((Chariot et al., Arthritis Rheum. 37(4):583-6 (1994)). Changes in the redox state of liver mitochondria can be investigated by measuring the arterial ketone body ratio (acetoacetate/3-hydroxybutyrate: AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic Acid (Lactate) Levels:

Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH Levels:

Measurement of NAD, NADP, NADH (NADH+H$^+$) or NADPH (NADPH+H$^+$) can be measured by a variety of fluorescent, enzymatic, or electrochemical techniques, e.g., the electrochemical assay described in US 2005/0067303.

Oxygen Consumption (vO$_2$ or VO2), Carbon Dioxide Output (vCO$_2$ or VCO2), and Respiratory Quotient (VCO2/VO2):

vO$_2$ is usually measured either while resting (resting vO$_2$) or at maximal exercise intensity (vO$_2$ max). Optimally, both values will be measured. However, for severely disabled patients, measurement of vO$_2$ max may be impractical. Measurement of both forms of vO$_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, Reduced Cytochrome C, and Ratio of Oxidized Cytochrome C to Reduced Cytochrome C:

Cytochrome C parameters, such as oxidized cytochrome C levels (Cyt C$_{ox}$), reduced cytochrome C levels (Cyt C$_{red}$), and the ratio of oxidized cytochrome C/reduced cytochrome C ratio (Cyt C$_{ox}$)/(Cyt C$_{red}$), can be measured by in vivo near infrared spectroscopy. See, e.g., Rolfe, P., "In vivo near-infrared spectroscopy," Ann. Rev. Biomed. Eng. 2:715-54 (2000) and Strangman et al., "Non-invasive neuroimaging using near-infrared light" Biol. Psychiatry 52:679-93 (2002).

Exercise Tolerance/Exercise Intolerance:

Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q (CoQ$^{red}$) levels, oxidized coenzyme Q (CoQ$^{ox}$) levels, total coenzyme Q (CoQ$^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention.

RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

TABLE 1

| Site of Dysfunction | Biochemical Event | Measurable, Energy Biomarker | Physical Effect |
| --- | --- | --- | --- |
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ H$^+$ gradient | Δ ATP | Organ dependent dysfunction |
| Respiratory Chain | ↓ Electron flux | Δ VO$_2$, RQ, BMR, ΔT, AT, pH | Metabolic dyscrasia & fatigue |
| Mitochondria & cytosol | ↓ ATP, ↓ VO$_2$ | Δ Work, ΔHR (CO) | Exercise intolerance |
| Mitochondria & cytosol | ↓ ATP | Δ PCr | Exercise intolerance |
| Respiratory Chain | ↓ Cyt C$_{Ox/Red}$ | Δ λ~700-900 nM (Near Infrared Spectroscopy) | Exercise intolerance |
| Intermediary metabolism | ↓ Catabolism | Δ C$^{14}$-Labeled substrates | Metabolic dyscrasia & fatigue |

TABLE 1-continued

| Site of Dysfunction | Biochemical Event | Measurable, Energy Biomarker | Physical Effect |
|---|---|---|---|
| Respiratory Chain | ↓ Electron flux | Δ Mixed Venous VO$_2$ | Metabolic dyscrasia & fatigue |
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ Glutathione$_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | Δ Isoprostane(s), eicasanoids | Uncertain |
| Cell membranes | Lipid oxidation | Δ Ethane (breath) | Uncertain |
| Cell membranes | Lipid oxidation | Δ Malondiaidehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one or any combination of the energy biomarkers described herein provide conveniently measurable benchmarks by which to gauge the effectiveness of treatment or suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications. They can be used in vitro, in vivo, or ex vivo experiments to modulate one or more energy biomarkers in an experimental system. Such experimental systems can be cell samples, tissue samples, cell components or mixtures of cell components, partial organs, whole organs, or organisms. Any one or more of the compounds of Formula I, Formula Ia, Formula Ib, Formula Ic, Formula Id and/or Formula Ie can be used in experimental systems or research applications. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject in which modulation of one or more energy biomarkers can be assayed; 2) administering one or more compounds of the invention to the cell sample or tissue sample; and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject in which modulation of one or more energy biomarkers can be assayed; 2) administering at least two compounds of the invention to the cell sample or tissue sample; 3) determining the amount of modulation of the one or more energy biomarkers after administration of the at least two compounds, compared to the status of the energy biomarker prior to administration of the at least compounds, and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins. Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee. "Diffusion-Controlled Matrix Systems", pp. 155-198 and Ron and Langer, "Erodible Systems", pp. 199-224, in "Treatise on Controlled Drug Delivery". A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing mitochondrial diseases. The invention also provides kits comprising any one or more of the compounds of Formula I, Formula Ia, Formula Ib, Formula Ic, Formula Id and/or Formula Ie. In some embodiments, the kit of the invention comprises the container described above.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following non-limiting examples.

EXAMPLES

Synthesis of Compounds

Example 1

2-(3-Hydroxy-3-methylbutyl)-3,5-dimethyl-6-(4-(trifluoromethyl)phenyl)cyclohexa-2,5-diene-1,4-dione Step 1: (2,6-Dimethyl-1,4-phenylene)bis(oxy)bis(methylene)dibenzene To a stirring solution of 2,6 dimethylhydroquinone (5 g, 36.2 mmol) in 50 mL dimethoxyethane at 23° C. was added a solution of elemental bromine (1.83 mL, 35.8 mmol) in 40 mL dimethoxyethane, dropwise over 75 min. After an additional 15 min, excess bromine was quenched with a 1 M aqueous solution of sodium thiosulfate (25 mL) and the resulting white emulsion was diluted in 150 mL EtOAc and 100 mL 1 M aqueous sodium bicarbonate. The organic layer was washed once with brine, and dried over anhydrous sodium sulfate. The solution was filtered and concentrated in vacuo to a brown solid. The residue was taken up in dimethylformamide (60 mL), and the resulting solution was degassed with Argon for 5 min, after which potassium carbonate (14.5 g, 105 mmol), and benzyl bromide (9.3 mL, 78 mmol) were added rapidly. The resulting suspension was stirred for 18 hr at 65° C. after which it was diluted in 400 mL methyl tertiary-butyl ether (MTBE), 200 mL hexanes, and 200 mL brine. The resulting emulsion was broken upon acidification to pH 4 with 1 M aqueous citric acid. The organics were removed, washed twice with 2.5 M aqueous ammonia, and once with brine (50 mL each). The remaining organics were dried over anhydrous sodium sulfate, filtered and concentrated in vacuo. Filtration on a silica gel plug (7% EtOAc/hexanes) yielded 2.8 g yellow solid, which was digested in 25 mL hexanes to produce 2.4 g yellow solid product, which was digested in 10% aqueous ethanol to produce the benzylated compound (2,6-dimethyl-1,4-phenylene)bis(oxy)bis(methylene)dibenzene, 7.7 g. $^1$H NMR (CDC$_3$, 400 MHz) 7.55-7.40 (m, 10H), 6.85 (s, 1H), 5.05 (s, 2H), 4.74 (s, 2H), 2.35 (s, 3H), 2.21 (s, 3H) ppm.

Step 2: 2,2,5,7-tetramethyl-8-(4-(trifluoromethyl)phenyl)chroman-6-ol

Into a 20-mL scintillation vial, the following solids were measured: (2,6-dimethyl-1,4-phenylene)bis(oxy)bis(methylene)dibenzene (400 mg, 1.01 mmol), 4-trifluoromethylphenylboronic acid (229 mg, 1.21 mmol), dichloro 1,1'-bis(diphenylphosphino)ferrocene palladium (II) dichloromethane adduct (22 mg, 30 µmol), and cesium fluoride (536 mg, 3.53 mmol). The solids were taken up in 10) mL ethanol, the flask was sealed, and the resulting mixture stirred at 60° C. After the reaction had stirred for 18 hr, the mixture was filtered, concentrated in vacuo. The residue was diluted in 50 ml. EtOAc, and washed with 20 mL each of 1 M aqueous citric acid and brine. The remaining organics were dried over anhydrous sodium sulfate, filtered and concentrated in vacuo. A crude purification was performed by filtration of the residue on silica gel plug (0→10% EtOAc/hexanes), yielding 300 mg of white solid that contained a mixture of the desired product and several small impurities. The resulting material was dissolved in a THF-ethanol mixture (3.5 mL, 1:1), charged with 5% palladium on carbon (73 mg, 35 µmol), and hydrogenated at ambient pressure. After stirring for 4 hr, the black suspension was filtered and concentrated in vacuo. The residue was rapidly dissolved in toluene (8 mL), degassed with Argon for 2 min. then charged with 2-methyl-3-buten-2-ol (170 µL, 1.6 mmol), and BF$_3$.OEt$_2$ (200 µL, 1.6 mmol). The resulting brown solution was stirred at 100° C. After 45 min, the reaction mixture was washed once with 1 M aqueous sodium bicarbonate, dried over anhydrous sodium sulfate, filtered and concentrated in vacuo. Purification by silica gel column chromatography (0→15% EtOAc/hexanes) afforded a yellow oil containing 2,2,5,7-tetramethyl-8-(4-(trifluoromethyl)phenyl)chroman-6-ol and some impurities (160 mg). $^1$H NMR (CDCl$_3$, 400 MHz) 7.6 (d, 2H), 7.3 (d, 2H), 4.25 (s, 1H), 2.65 (t, 2H), 2.17 (s, 3H), 1.94 (s, 3H), 1.75 (t, 2H), 1.16 (s, 6H) ppm.

Step 3: 2-(3-hydroxy-3-methylbutyl)-3,5-dimethyl-6-(4-(trifluoromethyl)phenyl)cyclohexa-2,5-diene-1,4-dione The purified residue containing 2,2,5,7-tetramethyl-8-(4-(trifluoromethyl)phenyl) chroman-6-ol from the above reaction (60 mg) was dissolved in THF/acetonitrile (1:1, 2 ml) and cooled in an ice-water bath. To the resulting solution was added dropwise an aqueous solution of ceric ammonium nitrate (170 mg, 310 µmol in 1 mL) until a reddish color persisted. When the titration endpoint was reached, the mixture was diluted in 5 mL EtOAc, washed once with brine (2 mL). The remaining organics were dried over anhydrous sodium sulfate, filtered and concentrated in vacuo. Purification by silica gel column chromatography (5→25% EtOAc/hexanes) producing 80 mg of 2-(3-hydroxy-3-methylbutyl)-3,5-dimethyl-6-(4-(trifluoromethyl)phenyl)cyclohexa-2,5-diene-1,4-dione, a yellow oil. $^1$H NMR (CDCl$_3$, 400 MHz) 7.67 (d, 2H), 7.26 (d, 2H), 2.60 (m, 2H), 2.11 (s, 3H), 1.92 (s, 3H), 1.54 (m, 2H), 1.25 (s, 6H) ppm.

Similarly, substituting in Step 2 4-trifluoromethylphenylboronic acid for other appropriate boronic acids, the following additional compounds were prepared.

Example 2

2-(3-Hydroxy-3-methylbutyl)-6-(4-methoxyphenyl)-3,5-dimethylcyclohexa-2,5-diene-1,4-dione $^1$H NMR (CDCl$_3$, 400 MHz) 7.07 (m, 3H), 6.93 (d, 2H), 3.82 (s, 3H), 2.59 (m, 2H), 2.09 (s, 3H), 1.96 (s, 3H), 1.55 (m, 2H), 1.25 (s, 6H) ppm.

Example 3

4-(5-(3-Hydroxy-3-methylbutyl)-2,4-dimethyl-3,6-dioxocyclohexa-1,4-dienyl)benzonitrile $^1$H NMR (CDCl$_3$, 400 MHz) 7.70 (d, 2H), 7.25 (d, 2H), 2.60 (m, 2H), 2.11 (s, 3H), 1.92 (s, 3H), 1.53 (m, 2H), 1.26 (s, 6H) ppm.

Example 4

2-(3-Hydroxy-3-methylbutyl)-3,5-dimethyl-6-(naphthalen-2-yl)cyclohexa-2,5-diene-1,4-dione $^1$H NMR (CDCl$_3$, 400 MHz) 7.86 (m, 3H), 7.61 (br s, 1H), 2.49 (m, 2H), 2.13 (s, 3H), 1.97 (s, 3H), 1.56 (m, 2H), 1.26 (s, 6H) ppm.

Example 5

2-(3,4-Difluorophenyl)-6-(3-hydroxy-3-methylbutyl)-3,5-dimethylcyclohexa-2,5-diene-1,4-dione $^1$H NMR (CDCl$_3$, 400 MHz) 7.20 (q, 1H), 6.98 (td, 1H), 6.86 (d, 1H), 2.60 (m, 2H), 2.10 (s, 3H), 1.94 (s, 3H), 1.53 (m, 2H), 1.26 (s, 6H) ppm.

Example 6

2-(4Fluorophenyl)-6-(3-hydroxy-3-methylbutyl)-3,5-dimethylcyclohexa-2,5-diene-1,4-dione $^1$H NMR (CDCl$_3$, 400 MHz) 7.15 (m, 4H), 2.60 (m, 2H), 2.10 (s, 3H), 1.93 (s, 3H), 1.54 (m, 2H), 1.25 (s, 6H) ppm.

Example 7

2-(4-chlorophenyl)-6-(3-hydroxo-3-methylbutyl)-3,5-dimethylcyclohexa-2,5-diene-1,4-dione $^1$H NMR (CDCl$_3$, 400 MHz) 7.40 (d, 2H), 7.09 (d, 2H), 2.62 (t, 2H), 2.11 (s, 3H), 1.95 (s, 3H), 1.55 (t, 2H), 1.34 (s, 1H), 1.27 (s, 6H) ppm.

Example 8

2-(2,3-dihydrobenzofuran-2-yl)-6-(3-hydroxy-3-methylbutyl)-3,5-dimethylcyclohexa-2,5-diene-1,4-dione $^1$H NMR (CDCl$_3$, 400 MHz) 7.64 (d, 1H), 7.51 (d, 1H), 7.30 (m, 2H), 6.55 (s, 1H), 2.64 (t, 2H), 2.37 (s, 3H), 2.08 (s, 3H), 1.57 (t, 2H), 1.37 (s, 1H), 1.30 (s, 6H) ppm.

Example 9

2-(4-Fluorophenyl)-3-(3-hydroxy-3-methylbutyl)-5,6-dimethylcyclohexa-2,5-diene-1,4-dione Step 1

(5-Bromo-2,3-dimethyl-1,4-phenylene)bis(oxy)bis(methylene)dibenzene

To a stirring solution of 2,3-dimethylbenzene-1,4-diol (5 g, 35.1 mmol) in 87.7 mL dimethoxyethane at 23° C. was added elemental bromine (1.83 mL, 35.8 mmol) dropwise over 5 min. After an additional 15 min (20 min total), excess bromine was quenched with a 1 M aqueous solution of sodium thiosulfate (25 mL) and the resulting white emulsion was diluted in 150 mL EtOAc and 100 mL H$_2$O. The organics were removed and washed twice with 1 M aqueous sodium bicarbonate, once with brine, and dried over anhydrous sodium sulfate. The solution was filtered and concentrated in vacuo to a brown solid. The residue was taken up in dimethylformamide (58 mL), and the resulting solution was degassed with argon for 5 min, after which potassium carbonate (14.5 g, 105 mmol), and benzyl bromide (9.3 mL, 78 mmol) were added rapidly. The resulting suspension was stirred for 18 hr. after which it was diluted in 200 mL EtOAc, 200 mL hexanes, and 200 mL H$_2$O. The resulting emulsion was broken upon acidification to pH 4 with 1 M aqueous citric acid. The organics were removed, then washed twice with H$_2$O, and once with brine (50 mL each). The remaining organics were dried over anhydrous sodium sulfate, filtered and concentrated in vacuo. Filtration on a silica gel plug (7% EtOAc/hexanes) yielded 2.8 g of a yellow solid, which was digested in 25 mL hexanes to produce 2.33 g of (5-bromo-2,3-dimethyl-1,4-phenylene)bis(oxy)bis(methylene)dibenzene as white solid product. $^1$H NMR (CDCl$_3$, 400 MHz) 7.55 (d, 2H), 7.40 (m, 8H), 7.0 (s, 1H), 5.00 (s, 2H), 4.80 (s, 2H), 2.21 (s, 3H), 2.15 (s, 31H) ppm.

Step 2

5-(4-fluorophenyl)-2,2,7,8-teramethylchroman-6-ol

Into a 20-mL scintillation vial, the following solids were measured: compound B (400 mg, 1.01 mmol), 4-fluorophenylboronic acid (170 mg, 1.21 mmol), dichloro 1,1'-bis(diphenylphosphino) ferrocene palladium (II) dichloromethane adduct (22 mg, 30 μmol), and cesium fluoride (536 mg, 3.53 mmol). The solids were taken up in 10 mL ethanol, the flask was sealed, and the resulting mixture stirred at 60° C. After the reaction had stirred for 18 hr. the mixture was filtered, diluted in 50 mL EtOAc, and washed with 20 mL each of 1 M aqueous sodium bicarbonate, saturated ammonium chloride, and brine. The remaining organics were dried over anhydrous sodium sulfate, filtered and concentrated in vacuo. A crude purification was performed by filtration of the residue on silica gel plug (0→10% EtOAc/hexanes), yielding 320 mg of white solid that contained a mixture of the desired product and several small impurities. The resulting material was dissolved in a THF-ethanol mixture (4 mL, 1:1), charged with 5% palladium on carbon (85 mg, 40 µmol), and hydrogenated at ambient pressure. After stirring for 4 hr. the black suspension was filtered and concentrated in vacuo. The residue was rapidly dissolved in toluene (8 mL), degassed with argon for 2 min, then charged with 2-methyl-3-buten-2-ol (250 µL, 2.4 mmol), and $BF_3 \cdot OEt_2$ (300 µL, 2.4 mmol). The resulting brown solution was stirred at 100° C. After 45 min, the reaction mixture was washed once with 1 M aqueous sodium bicarbonate, dried over anhydrous sodium sulfate, filtered and concentrated in vacuo. Purification by silica gel column chromatography (0→10% EtOAc/hexanes) afforded a yellow oil containing 5-(4-fluorophenyl)-2,2,7,8-tetramethylchroman-6-ol and some impurities (250 mg). $^1$H NMR (CDCl$_3$, 400 MHz) 7.3-7.1 (m, 41H), 4.25 (s, 1H), 2.28 (t, 2H), 2.17 (s, 3H), 2.14 (s, 3H), 1.65 (t, 2H), 1.26 (s, 6H) ppm.

Step 3

2-(4-Fluorophenyl)-3-(3-hydroxy-3-methylbutyl)-5,6-dimethylcyclohexa-2,5-diene-1,4-dione Purified residue containing 5-(4-fluorophenyl)-2,2,7,8-tetramethylchroman-6-ol from the above reaction (250 mg) was dissolved in acetonitrile (10 ml) and cooled in an ice-water bath. To the resulting solution was added dropwise aqueous solution of ceric ammonium nitrate (920 mg, 1.68 mmol in 10 mL) until a reddish color persisted. When the titration endpoint was reached, the mixture was diluted in 20 mL EtOAc, and washed once with brine (5 mL). The remaining organics were dried over anhydrous sodium sulfate, filtered and concentrated in vacuo. Purification by silica gel column chromatography (5→25% EtOAc/hexanes) producing 80 mg of 2-(4-fluorophenyl)-3-(3-hydroxy-3-methylbutyl)-5,6-dimethylcyclohexa-2,5-diene-1,4-dion, a yellow oil. $^1$H NMR (CDCl$_3$, 400 MHz) 7.09 (d, 4H), 2.40 (m, 2H), 2.07 (s, 3H), 2.04 (s, 3H), 1.50 (m, 2H), 1.10 (s, 6H) ppm.

Similarly by substituting 4-fluorophenylboronic acid for other aryl or heterocyclyl boronic acids, the following compounds were produced.

Example 10

2-(3-Hydroxy-3-methylbutyl)-5,6-dimethyl-3-phenylcyclohexa-2,5-diene-1,4-dione $^1$H NMR (CDCl$_3$, 400 MHz) 7.58 (m, 3H), 7.12 (d, 2H), 2.39 (m, 2H), 2.07 (s, 3H), 2.05 (s, 3H), 1.55 (m, 2H), 1.05 (s, 6H) ppm.

Example 11

2-(3-Hydroxy-3-methylbutyl)-5,6-dimethyl-3-(4-(trifluoromethyl)phenyl)cyclohexa-2,5-diene-1,4-dione $^1$H NMR (CDCl$_3$, 400 MHz) 7.67 (d, 2H), 7.25 (d, 2H), 2.38 (m, 2H), 2.08 (s, 3H), 2.05 (s, 3H), 1.49 (m, 2H), 1.09 (s, 6H) ppm.

Example 12

2-(3-Hydroxy-3-methylbutyl)-3-(4-methoxyphenyl)-5,6-dimethylcyclohexa-2,5-diene-1,4-dione $^1$H NMR (CDCl$_3$, 400 MHz) 7.05 (d, 2H), 6.93 (d, 2H), 2.42 (m, 2H), 2.05 (s, 3H), 2.02 (s, 3H), 1.51 (m, 2H), 1.10 (s, 6H) ppm.

Example 13

2-(3-Hydroxy-3-methylbutyl)-5,6-dimethyl-3-(naphthalen-2-yl)cyclohexa-2,5-diene-1,4-dione $^1$H NMR (CDCl$_3$, 400 MHz) 7.88-7.80 (m, 3H), 7.62 (s, 1H), 7.52-7.47 (m, 2H), 7.23-7.21 (m, 2H), 2.45 (m, 2H), 2.09 (s, 3H), 2.06 (s, 3H), 1.57 (m, 2H), 1.04 (s, 6H) ppm.

Example 14

2-(Benzofuran-2-yl)-3-(3-hydroxy-3-methylbutyl)-5,6-dimethylcyclohexa-2,5-diene-1,4-dione $^1$H NMR (CDCl$_3$, 400 MHz) 7.65 (d, 1H), 7.47 (d, 1H), 7.37 (s, 1H), 7.35-7.24 (m, 3H), 2.91 (m, 2H), 2.08 (s, 6H), 1.75 (m, 2H), 1.29 (s, 6H) ppm.

Example 15

2-(4-Chlorophenyl)-3-(3-hydroxy-3-methylbutyl)-5,6-dimethylcyclohexa-2,5-diene-1,4-dione $^1$H NMR (CDCl$_3$, 400 MHz) 7.85 (d, 2H), 7.06 (d, 2H), 2.39 (m, 2H), 2.06 (s, 3H), 2.04 (s, 3H), 1.49 (m, 2H), 1.10 (s, 6H) ppm.

Example 16

2-(4-Ethylphenyl)-3-(3-hydroxy-3-methylbutyl)-5,6-dimethylcyclohexa-2,5-diene-1,4-dione $^1$H NMR (CDCl$_3$, 400 MHz) 7.22 (d, 2H), 7.02 (d, 2H), 2.65 (q, 2H), 2.40 (m, 2H), 2.06 (s, 3H), 2.03 (s, 3H), 1.51 (m, 2H), 1.23 (t, 3H), 1.08 (s, 6H) ppm.

Example 17

2-(3-Hydroxy-3-methylbutyl)-5,6-dimethyl-3-(3-(trifluoromethyl)phenyl)cyclohexa-2,5-diene-1,4-dione $^1$H NMR (CDCl$_3$, 400 MHz) 7.66 (d, 1H), 7.54 (t, 1H), 7.40 (s, 1H), 7.32 (d, 1H), 2.37 (m, 2H), 2.07 (s, 3H), 2.05 (s, 3H), 1.51 (m, 2H), 1.08 (s, 6H) ppm.

Example 18

2-(4-tert-Butylphenyl)-3-(3-hydroxy-3-methylbutyl)-5,6-dimethylcyclohexa-2,5-diene-1,4-dione $^1$H NMR (CDCl$_3$, 400 MHz) 7.40 (d, 2H), 7.05 (d, 2H), 2.40 (m, 2H), 2.06 (s, 3H), 2.03 (s, 3H), 1.50 (m, 2H), 1.06 (s, 6H) ppm.

Example 19

2-(3-Hydroxy-3-methylbutyl)-5,6-dimethyl-3-(3-(trifluoromethyl)phenyl)cyclohexa-2,5-diene-1,4-dione $^1$H NMR (CDCl$_3$, 400 MHz) 7.70 (d, 2H), 7.23 (d, 2H), 2.37 (m, 2H), 2.07 (s, 3H), 2.04 (s, 3H), 1.49 (m, 2H), 1.09 (s, 6H) ppm.

Example 20

2-(3-Fluorophenyl)-3-(3-hydroxy-3-methylbutyl)-5,6-dimethylcyclohexa-2,5-diene-1,4-dione $^1$H NMR (CDCl$_3$, 400 MHz) 7.40 (m, 1H), 7.09 (m, 1H), 6.91-6.82 (m, 2H), 2.38 (m, 2H), 2.07 (s, 3H), 2.04 (s, 3H), 1.51 (m, 2H), 1.09 (s, 6H) ppm.

Example 21

2-(3,4-Difluorophenyl)-3-(3-hydroxy-3-methylbutyl)-5,6-dimethylcyclohexa-2,5-diene-1,4-dione $^1$H NMR (CDCl$_3$, 400 MHz) 7.38 (m, 1H), 7.21-7.06 (m, 2H), 2.38 (m, 2H), 2.07 (s, 3H), 2.05 (s, 3H), 1.48 (m, 2H), 1.07 (s, 3H), 1.06 (s, 3H) ppm.

Example 22

2-(2-Fluorophenyl)-3-(3-hydroxy-3-methylbutyl)-5,6-dimethylcyclohexa-2,5-diene-1,4-dione $^1$H NMR (CDCl$_3$, 400 MHz) 7.37 (m, 1H), 7.19 (m, 1H), 7.10 (m 2H), 2.38 (m, 2H), 2.07 (s, 3H), 2.05 (s, 3H), 1.48 (m, 2H), 1.07 (s, 3H), 1.05 (s, 3H) ppm.

Example 23

2-Benzyl-3-(3-hydroxy-3-methylbutyl)-5,6-dimethylcyclohexa-2,5-diene-1,4-dione $^1$H NMR (CDCl$_3$, 400 MHz) 7.26-7.22 (m, 3H), 7.18-7.14 (m, 2H), 3.87 (s, 2H), 2.60 (m, 2H), 2.00 (s, 6H), 1.37 (m, 2H), 1.19 (s, 6H) ppm.

Example 24

2-(3-Hydroxy-3-methylbutyl)-5,6-dimethyl-3-(3-phenylpropyl)cyclohexa-2,5-diene-1,4-dione $^1$H NMR (CDCl$_3$, 400 MHz 7.28-7.24 (m, 3H), 7.19-7.17 (m, 2H), 2.69 (t, 2H), 2.42 (m, 4H), 1.98 (m, 6H), 1.73 (m, 2H), 1.44 (m, 2H), 1.18 (s, 6H) ppm.

Example 25

2-(3-Hydroxy-3-methylbutyl)-5,6-dimethyl-3-phenethylcyclohexa-2,5-diene-1,4-dione $^1$H NMR (CDCl$_3$, 400 MHz) 7.29-7.23 (m, 3H), 7.20-7.18 (m, 2H), 2.73 (s, 2H), 2.41 (m, 2H), 2.00 (m, 6H), 1.39 (m, 2H), 1.21 (s, 6H) ppm.

Example 26

2-(1-Hydroxy-2-phenylethyl)-3-(3-hydroxy-3-methylbutyl)-5,6-dimethylcyclohexa-2,5-diene-1,4-dione $^1$H NMR (CDCl$_3$, 400 MHz) 7.28-7.14 (m, 5H), 4.81 (m, 1H), 3.69 (d, 1H), 2.38 (m, 1H), 2.19 (m, 1H), 2.02 (s, 3H), 2.00 (s, 3H), 1.32 (m, 1H), 1.15 (s, 6H), 1.05 (m, 1H) ppm.

BIOLOGICAL EXAMPLES

Example A

Screening Compounds of the Invention in Human Dermal Fibroblasts from Friedreich's Ataxia Patients An initial screen was performed to identify compounds effective for the amelioration of redox disorders. Test samples, 4 reference compounds (Idebenone, decylubiquinone, Trolox and α-tocopherol acetate), and solvent controls were tested for their ability to rescue FRDA fibroblasts stressed by addition of L-buthionine-(S,R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11 (24): 3055 (2002)). This specific BSO-mediated cell death can be prevented by administration of antioxidants or molecules involved in the antioxidant pathway, such as α-tocopherol, selenium, or small molecule glutathione peroxidase mimetics. However, antioxidants differ in their potency, i.e. the concentration at which they are able to rescue BSO-stressed FRDA fibroblasts.

MEM (a medium enriched in amino acids and vitamins, catalog no. 1-31F24-I) and Medium 199 (M199, catalog no. 1-21F22-I) with Earle's Balanced Salts, without phenol red, were purchased from Bioconcept. Fetal Calf Serum was obtained from PAA Laboratories. Basic fibroblast growth factor and epidermal growth factor were purchased from PeproTech. Penicillin-streptomycin-glutamine mix, L-buthionine (S,R)-sulfoximine, (+)-α-tocopherol acetate, decylubiquinone, and insulin from bovine pancreas were purchased from Sigma. Trolox (6-hydroxy-2,5,7,8-tetramethylchromane-2-carboxylic acid) was obtained from Fluka. Idebenone was obtained from Chemo Iberica. Calcein AM was purchased from Molecular Probes. Cell culture medium was made by combining 125 ml M 199 EBS, 50 ml Fetal Calf Serum, 100 U/ml penicillin, 100 μg/ml streptomycin, 2 mM glutamine, 10 μg/ml insulin, 10 ng/ml EGF, and 10 ng/ml bFGF; MEM EBS was added to make the volume up to 500 ml. A 10 mM BSO solution was prepared by dissolving 444 mg BSO in 200 ml of medium with subsequent filter-sterilization. During the course of the experiments, this solution was stored at +4° C. The cells were obtained from the Coriell Cell Repositories (Camden, N.J.; repository number GM04078) and grown in 10 cm tissue culture plates. Every third day, they were split at a 1:3 ratio.

The test samples were supplied in 1.5 ml glass vials. The compounds were diluted with DMSO, ethanol or PBS to result in a 5 mM stock solution. Once dissolved, they were stored at −20° C. Reference antioxidants (Idebenone, decylubiquinone, α-tocopherol acetate and trolox) were dissolved in DMSO.

Test samples were screened according to the following protocol: A culture with FRDA fibroblasts was started from a 1 ml vial with approximately 500,000 cells stored in liquid nitrogen. Cells were propagated in 10 cm cell culture dishes by splitting every third day in a ratio of 1:3 until nine plates were available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in a atmosphere with 95% humidity and 5% $CO_2$ to allow attachment of the cells to the culture plate.

MTP medium (243 µl) was added to a well of the microtiter plate. The test compounds were unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel (EXCEL is a registered trademark of Microsoft Corporation for a spreadsheet program) and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor did they have a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

The following table summarizes the $EC_{50}$ for the four control compounds.

| | $EC_{50}$ [µM] | | | | |
|---|---|---|---|---|---|
| Compound | Value 1 | Value 2 | Value 3 | Average | Stdev |
| Decylubiquinone | 0.05 | 0.035 | 0.03 | 0.038 | 0.010 |
| alpha-Tocopherol acetate | 0.4 | 0.15 | 0.35 | 0.30 | 0.13 |
| Idebenone | 1.5 | 1 | 1 | 1.2 | 0.3 |
| Trolox | 9 | 9 | 8 | 8.7 | 0.6 |

Certain compounds of the present invention such as:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
4-(5-(3-hydroxy-3-methylbutyl)-2,4-dimethyl-3,6-dioxocyclohexa-1,4-dienyl)benzonitrile;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione;
2-(4-fluorophenyl)-6-(3-hydroxy-3-methylbutyl)-3,5-dimethylcyclohexa-2,5-diene-1,4-dione; and
2-benzyl-3-(3-hydroxy-3-methylbutyl)-5,6-dimethylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(1-hydroxy-2-phenylethyl)-3-(3-hydroxy-3-methylbutyl)-5,6-dimethylcyclohexa-2,5-diene-1,4-dione;
2-(3-hydroxy-3-methylbutyl)-5,6-dimethyl-3-(4-(trifluoromethyl)-phenyl)cyclohexa-2,5-diene-1,4-dione;
2-(3-hydroxy-3-methylbutyl)-5,6-dimethyl-3-(naphthalen-2-yl)cyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2,5-diene-1,4-dione;
2-(4-tert-butylphenyl)-3-(3-hydroxy-3-methylbutyl)-5,6-dimethyl-cyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;
2-(3,4-difluorophenyl)-3-(3-hydroxy-3-methylbutyl)-5,6-dimethyl-cyclohexa-2,5-diene-1,4-dione; and
2-(4-chlorophenyl)-6-(3-hydroxy-3-methylbutyl)-3,5-dimethylcyclohexa-2,5-diene-1,4-dione.
exhibited protection against FRDA with an $EC_{50}$ of less than about 200 nM.

Example B

Screening Compounds of the Invention in Fibroblasts from Huntington's Patients

Compounds of the invention were tested using the screen as described in Example A, but substituting FRDA cells with Huntington's cells obtained from the Coriell Cell Repositories (Camden, N.J.; repository number GM 04281). The compounds were tested for their ability to rescue human dermal fibroblasts from Huntington's patients from oxidative stress.

Certain compounds of the present invention such as:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione;
2-(4-fluorophenyl)-6-(3-hydroxy-3-methylbutyl)-3,5-dimethylcyclohexa-2,5-diene-1,4-dione;
2-(3-hydroxy-3-methylbutyl)-5,6-dimethyl-3-phenethylcyclohexa-2,5-diene-1,4-dione;

2-benzyl-3-(3-hydroxy-3-methylbutyl)-5,6-dimethylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(1-hydroxy-2-phenylethyl)-3-(3-hydroxy-3-methylbutyl)-5,6-dimethylcyclohexa-2,5-diene-1,4-dione;
2-(3-hydroxy-3-methylbutyl)-3-(4-methoxyphenyl)-5,6-dimethyl-cyclohexa-2,5-diene-1,4-dione;
2-(3-hydroxy-3-methylbutyl)-5,6-dimethyl-3-(4-(trifluoromethyl)-phenyl)cyclohexa-2,5-diene-1,4-dione;
2-(3-hydroxy-3-methylbutyl)-5,6-dimethyl-3-(naphthalen-2-yl)cyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2,5-diene-1,4-dione;
2-(4-tert-butylphenyl)-3-(3-hydroxy-3-methylbutyl)-5,6-dimethyl-cyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;
4-(2-(3-hydroxy-3-methylbutyl)-4,5-dimethyl-3,6-dioxocyclohexa-1,4-dienyl)benzonitrile;
2-(3,4-difluorophenyl)-3-(3-hydroxy-3-methylbutyl)-5,6-dimethyl-cyclohexa-2,5-diene-1,4-dione;
2-(2-fluorophenyl)-3-(3-hydroxy-3-methylbutyl)-5,6-dimethylcyclohexa-2,5-diene-1,4-dione;
2-(3-hydroxy-3-methylbutyl)-3-(3-methoxyphenyl)-5,6-dimethyl-cyclohexa-2,5-diene-1,4-dione;
2-(4-fluoro-2-methoxyphenyl)-3-(3-hydroxy-3-methylbutyl)-5,6-dimethylcyclohexa-2,5-diene-1,4-dione;
2-(benzo[d][1,3]dioxol-5-yl)-3-(3-hydroxy-3-methylbutyl)-5,6-dimethylcyclohexa-2,5-diene-1,4-dione;
exhibited protection against Huntington's with an $EC_{50}$ of less than about 200 nM.

Example C

Screening Compounds of the Invention in Fibroblasts from Leber's Hereditary Optic Neuropathy Patients Compounds of the invention were screened as described in Example A, but substituting FRDA cells with Leber's Hereditary Optic Neuropathy (LHON) cells obtained from the Coriell Cell Repositories (Camden, N.J.; repository number GM03858). The compounds were tested for their ability to rescue human dermal fibroblasts from LHON patients from oxidative stress.

Certain compounds of the present invention such as:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
4-(5-(3-hydroxy-3-methylbutyl)-2,4-dimethyl-3,6-dioxocyclohexa-1,4-dienyl)benzonitrile;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione; and
2-(4-fluorophenyl)-6-(3-hydroxy-3-methylbutyl)-3,5-dimethylcyclohexa-2,5-diene-1,4-dione;
2-(3-hydroxy-3-methylbutyl)-5,6-dimethyl-3-phenethylcyclohexa-2,5-diene-1,4-dione;
2-benzyl-3-(3-hydroxy-3-methylbutyl)-5,6-dimethylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(3-hydroxy-3-methylbutyl)-3-(4-methoxyphenyl)-5,6-dimethylcyclohexa-2,5-diene-1,4-dione;
2-(3-hydroxy-3-methylbutyl)-5,6-dimethyl-3-(4-(trifluoromethyl)-phenyl)cyclohexa-2,5-diene-1,4-dione;
2-(3-hydroxy-3-methylbutyl)-5,6-dimethyl-3-(naphthalen-2-yl)cyclohexa-2,5-diene-1,4-dione;
2-(benzofuran-2-yl)-3-(3-hydroxy-3-methylbutyl)-5,6-dimethylcyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2,5-diene-1,4-dione;
2-(4-tert-butylphenyl)-3-(3-hydroxy-3-methylbutyl)-5,6-dimethyl-cyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;
2-(3,4-difluorophenyl)-3-(3-hydroxy-3-methylbutyl)-5,6-dimethyl-cyclohexa-2,5-diene-1,4-dione; and
2-(4-chlorophenyl)-6-(3-hydroxy-3-methylbutyl)-3,5-dimethylcyclohexa-2,5-diene-1,4-dione.
exhibited protection against LHON with an $EC_{50}$ of less than about 200 nM.

Example D

Screening Compounds of the Invention in Fibroblasts from Parkinson's Disease Patients Compounds of the invention were screened as described in Example A, but substituting FRDA cells with Parkinson's Disease (PD) cells obtained from the Coriell Cell Repositories (Camden, N.J.; repository number AG20439). The compounds were tested for their ability to rescue human dermal fibroblasts from Parkinson's disease patients from oxidative stress.

Certain compounds of the present invention such as:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
4-(5-(3-hydroxy-3-methylbutyl)-2,4-dimethyl-3,6-dioxocyclohexa-1,4-dienyl)benzonitrile;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione; and
2-(4-fluorophenyl)-6-(3-hydroxy-3-methylbutyl)-3,5-dimethylcyclohexa-2,5-diene-1,4-dione;
2-(3-hydroxy-3-methylbutyl)-5,6-dimethyl-3-phenethylcyclohexa-2,5-diene-1,4-dione;
2-(3-hydroxy-3-methylbutyl)-5,6-dimethyl-3-phenylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(1-hydroxy-2-phenylethyl)-3-(3-hydroxy-3-methylbutyl)-5,6-dimethylcyclohexa-2,5-diene-1,4-dione;
2-(3-hydroxy-3-methylbutyl)-5,6-dimethyl-3-(4-(trifluoromethyl)-phenyl)cyclohexa-2,5-diene-1,4-dione;

2-(3-hydroxy-3-methylbutyl)-5,6-dimethyl-3-(naphthalen-2-yl)cyclohexa-2,5-diene-1,4-dione;
2-(benzofuran-2-yl)-3-(3-hydroxy-3-methylbutyl)-5,6-dimethylcyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2,5-diene-1,4-dione;
2-(4-tert-butylphenyl)-3-(3-hydroxy-3-methylbutyl)-5,6-dimethyl-cyclohexa-2,5-diene-1,4-dione;
2-(3-fluorophenyl)-3-(3-hydroxy-3-methylbutyl)-5,6-dimethylcyclohexa-2,5-diene-1,4-dione;
exhibited protection against PD with an $EC_{50}$ of less than about 200 nM.

Example E

Screening Compounds of the Invention in Fibroblasts from CoQ10 Deficient Patients Compounds of the invention are tested using a screen similar to the one described in Example A, but substituting FRDA cells with cells obtained from CoQ10 deficient patients harboring a CoQ2 mutation. The compounds are tested for their ability to rescue human dermal fibroblasts from CoQ10 deficient patients from oxidative stress. Compounds of the present invention are considered active if they exhibit protection against CoQ10 deficiency with an $EC_{50}$ of less than about 200 nM.

Example F

Screening Compounds of the Invention in Human Dermal Fibroblasts from Autistic Patients A screen is performed to identify compounds effective for the amelioration of ASD. Test samples, and solvent controls were tested for their ability to rescue Autistic Syndrome Disorder (ASD) fibroblasts stressed by addition of L-buthionine-(S,R)-sulfoximine (BSO).

MEM (a medium enriched in amino acids and vitamins, catalog no. Gibco 11965) and Fetal Calf Serum are obtained from Invitrogen. Basic fibroblast growth factor and epidermal growth factor were purchased from PeproTech. Penicillin-streptomycin-glutamine mix. L-buthionine (S,R)-sulfoximine, and insulin from bovine pancreas were purchased from Sigma. Calcein AM was purchased from Molecular Probes. Cell culture medium (ATP) was made by combining 75 ml Fetal Calf Serum, 100 U/ml penicillin, 100 µg/ml streptomycin, 2 mM glutamine, 10 ng/ml EGF, and 10 ng/ml bFGF; MEM EBS is added to make the volume up to 500 ml. A 10 mM BSO solution was prepared by dissolving 444 mg BSO in 200 ml of medium with subsequent filter-sterilization. During the course of the experiments, this solution was stored at +4° C. The cells obtained from Dr. J. M. Shoffner, Medical Neurogenetics, Atlanta, Ga. were grown in 10 cm tissue culture plates. Every week, they were split at a 1:3 ratio.

The samples were supplied in 1.5 ml glass vials. The compounds were diluted with DMSO, ethanol or PBS to result in a 5 mM stock solution. Once dissolved, they were stored at −20° C.

The samples are screened according to the following protocol: A culture with ASD fibroblasts was started from a 1 ml vial with approximately 500,000 cells stored in liquid nitrogen. Cells were propagated in 10 cm cell culture dishes by splitting every week in a ratio of 1:3 until nine plates are available. Once confluent, fibroblasts were harvested. For 54 micro titer plates (96 well-MTP) a total of 14.3 million cells (passage eight) were re-suspended in 480 ml medium, corresponding to 100 µl medium with 3,000 cells/well. The remaining cells were distributed in 10 cm cell culture plates (500,000 cells/plate) for propagation. The plates were incubated overnight at 37° C. in an atmosphere with 95% humidity and 5% $CO_2$ to allow attachment of the cells to the culture plate.

MTP medium (243 µl) was added to a well of the microtiter plate. The test compounds are unfrozen, and 7.5 µl of a 5 mM stock solution was dissolved in the well containing 243 µl medium, resulting in a 150 µM master solution. Serial dilutions from the master solution were made. The period between the single dilution steps was kept as short as possible (generally less than 1 second).

Plates were kept overnight in the cell culture incubator. The next day, 10 µl of a 10 mM BSO solution were added to the wells, resulting in a 1 mM final BSO concentration. Forty-eight hours later, three plates were examined under a phase-contrast microscope to verify that the cells in the 0% control (wells E1-H1) were clearly dead. The medium from all plates was discarded, and the remaining liquid was removed by gently tapping the plate inversed onto a paper towel.

100 µl of PBS containing 1.2 µM Calcein AM were then added to each well. The plates were incubated for 50-70 minutes at room temperature. After that time the PBS was discarded, the plate gently tapped on a paper towel and fluorescence (excitation/emission wavelengths of 485 nm and 525 nm, respectively) was read on a Gemini fluorescence reader. Data was imported into Microsoft Excel® and used to calculate the $EC_{50}$ concentration for each compound.

The compounds were tested three times, i.e., the experiment was performed three times, the passage number of the cells increasing by one with every repetition.

The solvents (DMSO, ethanol, PBS) neither had a detrimental effect on the viability of non-BSO treated cells nor do they had a beneficial influence on BSO-treated fibroblasts even at the highest concentration tested (1%). None of the compounds showed auto-fluorescence. The viability of non-BSO treated fibroblasts was set as 100%, and the viability of the BSO- and compound-treated cells was calculated as relative to this value.

Certain compounds of the present invention were considered to be active if they exhibited protection against ASD with an $EC_{50}$ of less than 300 nM.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of reducing oxidative stress in a subject in need thereof, comprising administering to the subject a therapeutically effective amount of one or more compounds of Formula I:

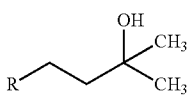

Formula I where,
R is selected from the group consisting of:

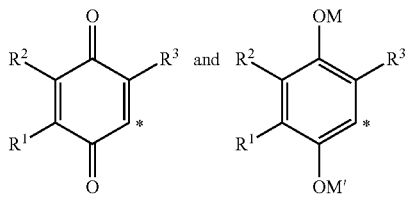

where the * indicates the point of attachment of R to the remainder of the molecule;
where M and M' are independently selected from the group consisting of hydrogen, —C(O)—R', —C(O)—$(C_2$-$C_6)$-alkenyl, —C(O)—$(C_2$-$C_6)$-alkynyl, —C(O)-aryl, —C(O)-heterocyclyl, —C(O)O—R', —C(O)NR'R'', —$SO_2$OR', —$SO_2$—$(C_1$-$C_6)$-alkyl, —$SO_2$—$(C_1$-$C_6)$-haloalkyl, —$SO_2$-aryl, —$SO_2$—NR'R'', —P(O)(OR')(OR''), and C-linked mono or di-peptide, where R' and R'' are each independently of each other hydrogen or $(C_1$-$C_6)$-alkyl optionally substituted with —OH, —$NH_2$, —NH$(C_1$-$C_4)$alkyl, —N$((C_1$-$C_4)$alkyl)$_2$, —C(O)—OH, —C(O)—O—$(C_1$-$C_4)$-alkyl or halogen;
where either
  $R^1$ is aryl-$(C_0$-$C_6)$-alkyl- or heterocyclyl-$(C_0$-$C_6)$-alkyl-, wherein the aryl or heterocyclyl is optionally substituted with one or more substituents selected from the group consisting of $(C_1$-$C_6)$-alkyl, $(C_2$-$C_6)$-alkenyl, $(C_2$-$C_6)$-alkynyl, halogen, $(C_1$-$C_6)$-haloalkyl, hydroxy, $(C_1$-$C_6)$-alkoxy, CN, nitro, —COOR$^4$, —NR$^5$R$^6$, —CONR$^5$R$^6$, thiol, $(C_1$-$C_6)$-thioalkyl, and —COR$^4$; and wherein when the $(C_0$-$C_6)$-alkyl group is $(C_1$-$C_6)$-alkyl then the $(C_1$-$C_6)$-alkyl is optionally substituted with OH, —O$(C_1$-$C_4)$-alkyl, —$NH_2$, —NH$(C_1$-$C_4)$-alkyl, —N$((C_1$-$C_4)$-alkyl)$_2$, oxo or halogen; and
  $R^2$ and $R^3$ are independently selected from the group consisting of hydrogen, halogen, $(C_1$-$C_6)$-alkyl and $(C_1$-$C_6)$-alkoxy;
or
  $R^3$ is aryl-$(C_0$-$C_6)$-alkyl- or heterocyclyl-$(C_0$-$C_6)$-alkyl-, wherein the aryl or heterocyclyl is optionally substituted with one or more substituents selected from the group consisting of $(C_1$-$C_6)$-alkyl, $(C_2$-$C_6)$-alkenyl, $(C_2$-$C_6)$-alkynyl, halogen, $(C_1$-$C_6)$-haloalkyl-, hydroxy, $(C_1$-$C_6)$-alkoxy, CN, nitro, —COOR$^4$, —NR$^5$R$^6$, —CONR$^5$R$^6$, thiol, $(C_1$-$C_6)$-thioalkyl-, and —COR$^4$; and wherein when the $(C_0$-$C_6)$-alkyl group is $(C_1$-$C_6)$-alkyl then the $(C_1$-$C_6)$-alkyl is optionally substituted with OH, —O$(C_1$-$C_4)$-alkyl, —$NH_2$, —NH$(C_1$-$C_4)$-alkyl, —N$((C_1$-$C_4)$-alkyl)$_2$, oxo or halogen; and
  $R^1$ and $R^2$ are independently selected from the group consisting of hydrogen, halogen, $(C_1$-$C_6)$-alkyl, and $(C_1$-$C_6)$-alkoxy;

where $R^4$ is hydrogen, $(C_1$-$C_6)$-alkyl, aryl, or aryl-$(C_1$-$C_6)$-alkyl-; and
where $R^5$ and $R^6$ are independently of each other hydroxy, $(C_1$-$C_6)$-alkoxy, $(C_1$-$C_6)$-alkyl, $(C_2$-$C_6)$-alkenyl, $(C_2$-$C_6)$-alkynyl, aryl, aryl-$(C_1$-$C_6)$-alkyl-, heterocyclyl, or heterocyclyl-$(C_1$-$C_6)$-alkyl-; wherein the alkyl, alkenyl, alkynyl, aryl and heterocyclyl groups are optionally further substituted with oxo, halogen, $(C_1$-$C_6)$-haloalkyl, hydroxy, $(C_1$-$C_6)$-alkoxy, or —COOR$^4$;
or a salt, a stereoisomer, or a mixture of stereoisomers thereof and additionally optionally comprising a pharmaceutically acceptable excipient.

2. The method according to claim 1 wherein R, in the one or more compounds, is

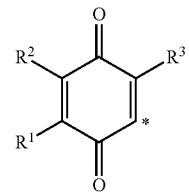

or a salt, a stereoisomer, or a mixture of stereoisomers thereof.

3. The method of claim 2 where, in the one or more compounds,
  $R^1$ is aryl-$(C_0$-$C_6)$-alkyl- or heterocyclyl-$(C_0$-$C_6)$-alkyl-, wherein the aryl or heterocyclyl is optionally substituted with one or more substituents selected from the group consisting of $(C_1$-$C_6)$-alkyl, $(C_2$-$C_6)$-alkenyl, $(C_2$-$C_6)$-alkynyl, halogen, $(C_1$-$C_6)$-haloalkyl, hydroxy, $(C_1$-$C_6)$-alkoxy, CN, nitro, —COOR$^4$, —NR$^5$R$^6$, —CONR$^5$R$^6$, thiol, $(C_1$-$C_6)$-thioalkyl, and —COR$^4$; and wherein when the $(C_0$-$C_6)$-alkyl group is $(C_1$-$C_6)$-alkyl then the $(C_1$-$C_6)$-alkyl is optionally substituted with OH, —O$(C_1$-$C_4)$-alkyl, —$NH_2$, —NH$(C_1$-$C_4)$-alkyl, —N$((C_1$-$C_4)$-alkyl)$_2$, oxo or halogen; and
  $R^2$ and $R^3$ are independently selected from the group consisting of hydrogen, halogen, $(C_1$-$C_6)$-alkyl, and $(C_1$-$C_6)$-alkoxy;
or a salt, a stereoisomer, or a mixture of stereoisomers thereof.

4. The method of claim 3 where, in the one or more compounds, $R^2$ and $R^3$ are $(C_1$-$C_6)$-alkyl; or a salt, a stereoisomer, or a mixture of stereoisomers thereof.

5. The method of claim 3 where, in the one or more compounds, le is aryl-$(C_0$-$C_6)$-alkyl-, wherein the aryl is optionally substituted with one or more substituents selected from the group consisting of $(C_1$-$C_6)$-alkyl, halogen, $(C_1$-$C_6)$-haloalkyl, hydroxy, $(C_1$-$C_6)$-alkoxy, CN, —COOR$^4$, and —COR$^4$; or a salt, a stereoisomer, or a mixture of stereoisomers thereof.

6. The method of claim 3 where, in the one or more compounds, le is heterocyclyl-$(C_0$-$C_6)$-alkyl-, wherein the heterocyclyl is optionally substituted with one or more substituents independently selected from the group consisting of $(C_1$-$C_6)$-alkyl, halogen, $(C_1$-$C_6)$-haloalkyl, hydroxy, $(C_1$-$C_6)$-alkoxy, CN, nitro, —COOR$^4$, —NR$^5$R$^6$, —CONR$^5$R$^6$, and —COR$^4$; or a salt, a stereoisomer, or a mixture of stereoisomers thereof.

7. The method of claim 2 where, in the one or more compounds,

R¹ and R² are independently selected from the group consisting of hydrogen, halogen, ($C_1$-$C_6$)-alkyl and ($C_1$-$C_6$)-alkoxy; and R³ is aryl-($C_0$-$C_6$)-alkyl- or heterocyclyl-($C_0$-$C_6$)-alkyl-, wherein the aryl or heterocyclyl is optionally substituted with one or more substituents independently selected from the group consisting of ($C_1$-$C_6$)-alkyl, ($C_2$-$C_6$)-alkenyl, ($C_2$-$C_6$)-alkynyl, halogen, ($C_1$-$C_6$)-haloalkyl-, hydroxy, ($C_1$-$C_6$)-alkoxy, CN, nitro, —COOR⁴, —NR⁵R⁶, —CONR⁵R⁶, thiol, ($C_1$-$C_6$)-thioalkyl-, and —COR⁴; and wherein when the ($C_0$-$C_6$)-alkyl group is ($C_1$-$C_6$)-alkyl then the ($C_1$-$C_6$)-alkyl is optionally substituted with OH, —O($C_1$-$C_4$)-alkyl, —NH₂, —NH($C_1$-$C_4$)-alkyl, —N(($C_1$-$C_4$)-alkyl)₂, oxo or halogen;

or a salt, a stereoisomer, or a mixture of stereoisomers thereof.

8. The method of claim 7 where, in the one or more compounds, R¹ and R² are ($C_1$-$C_6$)-alkyl; or a salt, a stereoisomer, or a mixture of stereoisomers thereof.

9. The method of claim 7 where, in the one or more compounds, R³ is aryl-($C_0$-$C_6$)-alkyl-, wherein the aryl is optionally substituted with one or more substituents independently selected from the group consisting of ($C_1$-$C_6$)-alkyl, halogen, ($C_1$-$C_6$)-haloalkyl, hydroxy, ($C_1$-$C_6$)-alkoxy, CN, —COOR⁴, and —COR⁴; or a salt, a stereoisomer, or a mixture of stereoisomers thereof.

10. The method of claim 7 where, in the one or more compounds, R³ is heterocyclyl-($C_0$-$C_6$)-alkyl-, wherein the heterocyclyl is optionally substituted with one or more substituents independently selected from the group consisting of ($C_1$-$C_6$)-alkyl, halogen, ($C_1$-$C_6$)-haloalkyl, hydroxy, ($C_1$-$C_6$)-alkoxy, CN, nitro, —COOR⁴, —NR⁵R⁶, —CONR⁵R⁶, and —COR⁴; or a salt, a stereoisomer, or a mixture of stereoisomers thereof.

11. The method according to claim 3 where, in the one or more compounds, R¹ is phenyl mono-substituted with a substituent selected from the group consisting of fluoro, chloro, and trifluoromethyl.

12. The method according to claim 7 where, in the one or more compounds, R³ is phenyl mono-substituted with a substituent selected from the group consisting of fluoro, chloro, and trifluoromethyl.

13. The method according to claim 1 wherein the one or more compounds are selected from the group consisting of:
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
4-(5-(3-hydroxy-3-methylbutyl)-2,4-dimethyl-3,6-dioxocyclohexa-1,4-dienyl)benzonitrile;
2-(3-hydroxy-3-methylbutyl)-3,5-dimethyl-6-(naphthalen-2-yl)cyclohexa-2,5-diene-1,4-dione;
2-(3,4-difluorophenyl)-6-(3-hydroxy-3-methylbutyl)-3,5-dimethylcyclohexa-2,5-diene-1,4-dione;
2-(4-fluorophenyl)-6-(3-hydroxy-3-methylbutyl)-3,5-dimethylcyclohexa-2,5-diene-1,4-dione;
2-(4-chlorophenyl)-6-(3-hydroxy-3-methylbutyl)-3,5-dimethylcyclohexa-2,5-diene-1,4-dione;
2-(2,3-dihydrobenzofuran-2-yl)-6-(3-hydroxy-3-methylbutyl)-3,5-dimethylcyclohexa-2,5-diene-1,4-dione;
2-(3-hydroxy-3-methylbutyl)-5,6-dimethyl-3-phenethylcyclohexa-2,5-diene-1,4-dione;
2-(3-hydroxy-3-methylbutyl)-5,6-dimethyl-3-phenylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(1-hydroxy-2-phenylethyl)-3-(3-hydroxy-3-methylbutyl)-5,6-dimethylcyclohexa-2,5-diene-1,4-dione;
2-(3-hydroxy-3-methylbutyl)-3-(4-methoxyphenyl)-5,6-dimethyl-cyclohexa-2,5-diene-1,4-dione;
2-(3-hydroxy-3-methylbutyl)-5,6-dimethyl-3-(4-(trifluoromethyl)-phenyl)cyclohexa-2, 5-diene-1,4-dione;
2-(3-hydroxy-3-methylbutyl)-5,6-dimethyl-3-(naphthalen-2-yl)cyclohexa-2,5-diene-1,4-dione;
2-(benzofuran-2-yl)-3-(3-hydroxy-3-methylbutyl)-5,6-dimethylcyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)-cyclohexa-2, 5-diene-1,4-dione;
2-(4-tert-butylphenyl)-3-(3-hydroxy-3-methylbutyl)-5,6-dimethyl-cyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;
4-(2-(3-hydroxy-3-methylbutyl)-4,5-dimethyl-3,6-dioxocyclohexa-1,4-dienyl)benzonitrile;
2-(3,4-difluorophenyl)-3-(3-hydroxy-3-methylbutyl)-5,6-dimethyl-cyclohexa-2,5-diene-1,4-dione;
2-(2-fluorophenyl)-3-(3-hydroxy-3-methylbutyl)-5,6-dimethylcyclohexa-2,5-diene-1,4-dione;
2-(3-hydroxy-3-methylbutyl)-3-(3-methoxyphenyl)-5,6-dimethyl-cyclohexa-2,5-diene-1,4-dione;
2-(4-fluoro-2-methoxyphenyl)-3-(3-hydroxy-3-methylbutyl)-5,6-dimethylcyclohexa-2, 5-diene-1,4-dione;
2-(benzo[d][1,3]dioxol-5-yl)-3-(3-hydroxy-3-methylbutyl)-5,6-dimethylcyclohexa-2, 5-diene-1,4-dione;
2-(2,4-difluorophenyl)-3-(3-hydroxy-3-methylbutyl)-5,6-dimethylcyclohexa-2,5-diene-1,4-dione;
2-(3,5-bis(trifluoromethyl)phenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(2-(thiazol-2-yl)ethyl)cyclohexa-2,5-diene-1,4-dione;
2-(3-hydroxy-3-methylbutyl)-5,6-dimethyl-3-(2-(thiazol-5-yl)ethyl)cyclohexa-2,5-diene-1,4-dione;
2-(3-hydroxy-3-methylbutyl)-5,6-dimethyl-3-(2-(pyridin-2-yl)ethyl)cyclohexa-2,5-diene-1,4-dione;
2-(3-hydroxy-3-methylbutyl)-5,6-dimethyl-3-(2-(pyridazin-4-yl)ethyl)cyclohexa-2,5-diene-1,4-dione;
2-(3-hydroxy-3-methylbutyl)-5,6-dimethyl-3-(2-(thiophen-2-yl)ethyl)cyclohexa-2,5-diene-1,4-dione;
2-(3-hydroxy-3-methylbutyl)-5,6-dimethyl-3-(2-(thiophen-3-yl)ethyl)cyclohexa-2,5-diene-1,4-dione;
2-(2-(furan-2-yl)ethyl)-3-(3-hydroxy-3-methylbutyl)-5,6-dimethylcyclohexa-2,5-diene-1,4-dione;
2-(2-(furan-3-yl)ethyl)-3-(3-hydroxy-3-methylbutyl)-5,6-dimethylcyclohexa-2,5-diene-1,4-dione;
2-(2-(1H-pyrazol-5-yl)ethyl)-3-(3-hydroxy-3-methylbutyl)-5,6-dimethylcyclohexa-2, 5-diene-1,4-dione;
2-(2-(1H-pyrazol-4-yl)ethyl)-3-(3-hydroxy-3-methylbutyl)-5,6-dimethylcyclohexa-2, 5-diene-1,4-dione;
2-(2-(1H-pyrazol-1-yl)ethyl)-3-(3-hydroxy-3-methylbutyl)-5,6-dimethylcyclohexa-2,5-diene-1,4-dione;
2-(2-(1H-imidazol-5-yl)ethyl)-3-(3-hydroxy-3-methylbutyl)-5,6-dimethylcyclohexa-2,5-diene-1,4-dione;
2-(2-(1H-imidazol-2-yl)ethyl)-3-(3-hydroxy-3-methylbutyl)-5,6-dimethylcyclohexa-2,5-diene-1,4-dione;
2-(3-hydroxy-3-methylbutyl)-5,6-dimethyl-3-(2-(oxazol-5-yl)ethyl)cyclohexa-2,5-diene-1,4-dione;

2-(3-hydroxy-3-methylbutyl)-5,6-dimethyl-3-(2-(oxazol-2-yl)ethyl)cyclohexa-2,5-diene-1,4-dione;

2-(3-hydroxy-3-methylbutyl)-5,6-dimethyl-3-(2-(oxazol-4-yl)ethyl)cyclohexa-2,5-diene-1,4-dione; and 2-(2-(1H-indol-3-yl)ethyl)-3-(3-hydroxy-3-methylbutyl)-5,6-dimethylcyclohexa-2,5-diene-1,4-dione;

or a salt, stereoisomer, or mixture of stereoisomers thereof.

14. The method according to claim 1, wherein the one or more compounds are selected from the group consisting of:

2-(3-hydroxy-3-methylbutyl)-3,5-dimethyl-6-(4-(trifluoromethyl)phenyl)cyclohexa-2,5-diene-1,4-dione;

2-(3-hydroxy-3-methylbutyl)-5,6-dimethyl-3-(4-(trifluoromethyl)-phenyl)cyclohexa-2,5-diene-1,4-dione;

2-(4-chlorophenyl)-3-(3-hydroxy-3-methylbutyl)-5,6-dimethylcyclohexa-2,5-diene-1,4-dione; and 2-(4-chlorophenyl)-6-(3-hydroxy-3-methylbutyl)-3,5-dimethylcyclohexa-2,5-diene-1,4-dione; and or a salt thereof.

15. The method of claim 1, where the subject in need thereof has a mitochondrial disorder, wherein the mitochondrial disorder is selected from the group consisting of an inherited mitochondrial disease; Myoclonic Epilepsy with Ragged Red Fibers (MERRF); Mitochondrial Myopathy; Encephalopathy; Lactacidosis; Stroke (MELAS); Leber's Hereditary Optic Neuropathy (LHON); chronic progressive external ophthalmoplegia (CPEO); Leigh Disease; Kearns-Sayre Syndrome (KSS); Friedreich's Ataxia (FA); Co-Enzyme Q10 Deficiency; Complex I Deficiency; Complex II Deficiency; Complex III Deficiency; Complex IV Deficiency; Complex V Deficiency; Parkinson's disease; Alzheimer's disease; amyotrophic lateral sclerosis (ALS); muscular dystrophy; Huntington's disease; a pervasive developmental disorder; epilepsy; macular degeneration; diabetes; cancer; a cerebral vascular accident; autism; myopathy; cardiomyopathy; renal tubular acidosis; neurodegenerative diseases; motor neuron diseases; other neurological diseases; genetic diseases; mood disorders; schizophrenia; bipolar disorder; age-associated diseases; cerebral vascular diseases; autistic disorder (ASD); Asperger's disorder; childhood disintegrative disorder (CDD); Rett's disorder; PDD-Not Otherwise Specified (PDD-NOS); Mitochondrial encephalomyopathy, lactic acidosis, and stroke-like episodes (MELAS); neuronal injury associated with seizures; and neuronal injury associated with ischemia.

16. The method of claim 2, where the subject in need thereof has a mitochondrial disorder, wherein the mitochondrial disorder is selected from the group consisting of an inherited mitochondrial disease; Myoclonic Epilepsy with Ragged Red Fibers (MERRF); Mitochondrial Myopathy; Encephalopathy; Lactacidosis; Stroke (MELAS); Leber's Hereditary Optic Neuropathy (LHON); chronic progressive external ophthalmoplegia (CPEO); Leigh Disease; Kearns-Sayre Syndrome (KSS); Friedreich's Ataxia (FA); Co-Enzyme Q10 Deficiency; Complex I Deficiency; Complex II Deficiency; Complex III Deficiency; Complex IV Deficiency; Complex V Deficiency; Parkinson's disease; Alzheimer's disease; amyotrophic lateral sclerosis (ALS); muscular dystrophy; Huntington's disease; a pervasive developmental disorder; epilepsy; macular degeneration; diabetes; cancer; and a cerebral vascular accident; autism; myopathy; cardiomyopathy; renal tubular acidosis; neurodegenerative diseases; motor neuron diseases; other neurological diseases; genetic diseases; mood disorders; schizophrenia; bipolar disorder; age-associated diseases; cerebral vascular diseases; autistic disorder (ASD); Asperger's disorder; childhood disintegrative disorder (CDD); Rett's disorder; PDD-Not Otherwise Specified (PDD-NOS); Mitochondrial encephalomyopathy, lactic acidosis, and stroke-like episodes (MELAS); neuronal injury associated with seizures; and neuronal injury associated with ischemia.

17. The method of claim 15, wherein the mitochondrial disorder is selected from the group consisting of Parkinson's disease; Alzheimer's disease; Huntington's disease; epilepsy; amyotrophic lateral sclerosis (ALS); and macular degeneration.

* * * * *

UNITED STATES PATENT AND TRADEMARK OFFICE
CERTIFICATE OF CORRECTION

PATENT NO. : 9,486,435 B2
APPLICATION NO. : 14/586516
DATED : November 8, 2016
INVENTOR(S) : Andrew W. Hinman et al.

It is certified that error appears in the above-identified patent and that said Letters Patent is hereby corrected as shown below:

In the Claims

Claim 5, Column 54, Line 52:
Please change "compounds, le is aryl-($C_0$-$C_6$)-alkyl-, wherein the aryl is" to --compounds, $R^1$ is aryl-($C_0$-$C_6$)-alkyl-, wherein the aryl is--

Claim 6, Column 54, Line 59:
Please change "compounds, le is heterocyclyl-($C_0$-$C_6$)-alkyl-, wherein the" to --compounds, $R^1$ is heterocyclyl-($C_0$-$C_6$)-alkyl-, wherein the--

Signed and Sealed this
Twenty-first Day of March, 2017

Michelle K. Lee
*Director of the United States Patent and Trademark Office*